(12) United States Patent
Ahn

(10) Patent No.: US 10,717,984 B2
(45) Date of Patent: Jul. 21, 2020

(54) METHOD FOR CONTROLLING FLOWERING TIME BY REGULATING OF SVP-FLM-β PROTEIN COMPLEX FORMATION

(71) Applicant: Korea University Research and Business Foundation, Seoul (KR)

(72) Inventor: Ji Hoon Ahn, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 1211 days.

(21) Appl. No.: 14/484,816

(22) Filed: Sep. 12, 2014

(65) Prior Publication Data
US 2015/0197761 A1      Jul. 16, 2015

(30) Foreign Application Priority Data

Jan. 15, 2014   (KR) .................. 10-2014-0005283

(51) Int. Cl.
*C12N 15/82* (2006.01)

(52) U.S. Cl.
CPC ....... *C12N 15/827* (2013.01); *C12N 15/8218* (2013.01)

(58) Field of Classification Search
None
See application file for complete search history.

(56) References Cited

U.S. PATENT DOCUMENTS

2008/0263726 A1* 10/2008 Lee .................. C07K 14/415
800/278

OTHER PUBLICATIONS

Li et al. Developmental cell 15.1 (2008): 110-120.*
Chen et al. The Plant Journal 82.2 (2015): 302-314.*
Shitsukawa et al. Physiologia Plantarum 130.4 (2007): 627-636.*
Trevaskis et al. Plant Physiology, Jan. 2007, vol. 143, pp. 225-235.*
Masiero, et al., 2004. Development 131: 5981-5990.*
Alonso et al., Science vol. 301(1) Aug. 2003.*
Lee et al. Science 342.6158 (2013): 628-632.*
Yang et al. (Plant Physiology (2015): pp. 00307). (Year: 2015).*
Pose, D., et al., "Temperature-Dependent Regulation of Flowering by Antagonistic FLM Variants", "Nature", Nov. 21, 2013, pp. 414-417, vol. 503.
Aoyama, T., et al., "A glucocorticoid-mediated transcriptional induction system in transgenic plants", "The Plant Journal", 1997, pp. 605-612, vol. 11, No. 3.
Ausin, I., et al., "Regulation of flowering time by FVE, a retinoblastoma-associated protein", "Nature Genetics", Feb. 2004, pp. 162-166, vol. 36, No. 2.
Baeurle, I., et al., "Widespread Role for the Flowering-Time Regulators FCA and FPA in RNA-Mediated Chromatin Silencing", "Science", Oct. 5, 2007, pp. 109-112, vol. 318.
Balasubramanian, S., et al., "Potent Induction of *Arabidopsis thaliana* Flowering by Elevated Growth Temperature", "PLoS Genetics", Jul. 2006, pp. e106, 0980-0989, vol. 2, No. 7.
Cook, B., et al., "Divergent responses to spring and winter warming drive community level flowering trends", "PNAS", Jun. 5, 2012, pp. 9000-9005, vol. 109, No. 23.
Craufurd, P., et al., "Climate change and the flowering time of annual crops", "Journal of Experimental Botany", 2009, pp. 2529-2539, vol. 60, No. 9.
Fire, A., et al., "Potent and specific genetic interference by double-stranded RNA in Caenorhabditis elegans", "Nature", Feb. 19, 1998, pp. 806-811, vol. 391.
Fitter, A., et al., "Rapid Changes in Flowering Time in British Plants", "Science", May 31, 2002, pp. 1689-1691, vol. 296.
Kim, J., et al., "The microRNA156-Squamosa Promoter Binding Protein-Like3 Module Regulates Ambient Temperature-Responsive Flowering via Flowering Locus T in *Arabidopsis* ", "Plant Physiology", May 2012, pp. 461-478, vol. 159.
Kim, H., et al., "A genetic link between cold responses and flowering time through FVE in *Arabidopsis thaliana*", "Nature Genetics", Feb. 2004, pp. 167-171, vol. 36, No. 2.
Lee, I., et al., "Isolation of Luminidependens: A Gene Involved in the Control of Flowering Time in *Arabidopsis*", "The Plant Cell", Jan. 1994, pp. 75-83, vol. 6.
Lee, H., et al., "The Agamous-Like 20 MADS domain protein integrates floral inductive pathways in *Arabidopsis*", "Genes Dev.", 2000, pp. 2366-2376, vol. 14.
Lee, J., et al., "Regulation of Temperature-Responsive Flowering by MADS-Box Transcription Factor Repressors", "Science Express", Sep. 12, 2013, pp. 1-8.
Lee, J., et al., "Role of SVP in the control of flowering time by ambient temperature in *Arabidopsis*", "Genes Dev.", 2007, pp. 397-402, vol. 21.
Lim, M., et al., "A New *Arabidopsis* Gene, FLK, Encodes an RNA Binding Protein with K Homology Motifs and Regulated Flowering Time via Flowering Locus C", "The Plant Cell", Mar. 2004, pp. 731-740, vol. 16.
Michaels, S., et al., "Flowering Locus C Encodes a Novel MADS Domain Protein That Acts as a Repressor of Flowering", "The Plant Cell", May 1999, pp. 949-956, vol. 11.
Moloney, M., et al., "High efficiency transformation of *Brassica napus* using Agrobacterium vectors", "Plant Cell Reports", 1989, pp. 238-242, vol. 8.

(Continued)

*Primary Examiner* — Charles Logsdon
(74) *Attorney, Agent, or Firm* — Hultquist, PLLC; Steven J. Hultquist

(57) ABSTRACT

The present invention relates to a method of controlling the flowering time of a plant by regulating the formation of the SVP-FLM-β protein complex, based on the finding that the SVP-FLM-β protein complex is a regulating factor for plant flowering that senses small changes in ambient temperature. The FLM-β RNAi and SVP RNAi for controlling flowering time according to the present invention can be used to control flowering time by inhibiting the expression of FLM-β and SVP or regulating the interaction therebetween, and thus, they can prevent a decrease in crop production or a change in the ecosystem from being caused by a sudden change in temperature.

2 Claims, 11 Drawing Sheets
Specification includes a Sequence Listing.

(56) References Cited

OTHER PUBLICATIONS

Poethig, R., "Phase Change and the Regulation of Shoot Morphogenesis in Plants", "Science", Nov. 16, 1990, pp. 923-930, vol. 250.

Schomburg, F., et al., "FPA, a Gene Involved in Floral Induction in *Arabidopsis*, Encodes a Protein Containing RNA-Recongnition Motifs", "The Plant Cell", Jun. 2001, pp. 1427-1436, vol. 13.

Scortecci, K., et al., "Identification of a MADS-box gene, Flowering Locus M, that represses flowering", "The Plant Journal", 2001, pp. 229-236, vol. 26.

Sharma, P., et al., "The molecular biology of the low-temperature response in plants", "BioEssays", 2005, pp. 1048-1059, vol. 27.

Simpson, G., et al., "FY Is an RNA 3' End-Processing Factor that Interacts with FCA to Control the *Arabidopsis* Floral Transition", "Cell", Jun. 13, 2003, pp. 777-787, vol. 113.

Yamaguchi, A., et al., "Twin Sister of FT (TSF) Acts as a Floral Pathway Integrator Redundantly with FT", "Plant Cell Physiol.", 2005, pp. 1175-1189, vol. 46, No. 8.

Yoo, S., et al., "Constans Activates Suppressor of Overexpression of Constans 1 through Flowering Locus T to Promote Flowering in *Arabidopsis*", "Plant Physiology", Oct. 2005, pp. 770-778, vol. 139.

Gandikota, M., et al., "The miRNA156/157 recognition element in the 3' UTR of the *Arabidopsis* SBP box gene SPL3 prevents early flowering by translational inhibition in seedinglings", "The Plant Journal", 2007, pp. 683-693, vol. 49, Publisher: Blackwell Publishing Lts.

Sunkar, R., et al., "Novel and Stress-Regulated MicroRNAs and Other Small RNAs from *Arabidopsis*", "The Plant Cell", Aug. 2004, pp. 2001-2019, vol. 16, Publisher: www.plantcell.org, American Society of Plant Biologists.

\* cited by examiner

FIG. 2

| Genotype | RLN | CLN | TLN | TLN StDev | TLN range | n |
|---|---|---|---|---|---|---|
| Experiment 1 (27°C, long days) | | | | | | |
| Col (wild-type) | 10.2 | 3.0 | 13.2 | ±1.9 | 11–17 | 15 |
| svp-32 | 7.8 | 1.6 | 9.4 | ±0.7 | 8–10 | 18 |
| flm-3 | 8.7 | 3.1 | 11.8 | ±0.8 | 11–13 | 16 |
| flc-3 | 9.9 | 2.4 | 12.3 | ±1.6 | 10–14 | 20 |
| Experiment 2 (23°C, long days) | | | | | | |
| Col (wild-type) | 13.3 | 3.4 | 16.7 | ±0.9 | 15–19 | 30 |
| svp-32 | 7.8 | 2.0 | 9.8 | ±0.5 | 9–10 | 42 |
| flm-3 | 8.6 | 2.9 | 11.5 | ±0.5 | 11–12 | 38 |
| flc-3 | 10.9 | 2.6 | 13.5 | ±1.1 | 12–16 | 37 |
| Experiment 3 (16°C, long days) | | | | | | |
| Col (wild-type) | 25.6 | 5.8 | 31.4 | ±1.0 | 30–34 | 35 |
| svp-32 | 8.6 | 2.5 | 11.1 | ±0.7 | 10–12 | 34 |
| flm-3 | 9.4 | 2.5 | 11.9 | ±0.9 | 11–14 | 33 |
| flc-3 | 20.5 | 4.8 | 25.3 | ±1.4 | 23–28 | 35 |
| Experiment 4 (10°C, long days) | | | | | | |
| Col (wild-type) | 33.2 | 7.8 | 41.0 | ±2.6 | 38–46 | 26 |
| svp-32 | 10.4 | 2.7 | 13.1 | ±0.9 | 12–15 | 27 |
| flm-3 | 15.6 | 4.5 | 20.1 | ±1.2 | 17–22 | 27 |
| flc-3 | 25.0 | 5.6 | 30.6 | ±1.5 | 28–32 | 26 |
| Experiment 5 (5°C, long days) | | | | | | |
| Col (wild-type) | 26.2 | 6.2 | 32.4 | ±1.5 | 30–34 | 18 |
| svp-32 | 8.6 | 1.9 | 10.5 | ±2.2 | 9–14 | 22 |
| flm-3 | 15.4 | 4.0 | 19.4 | ±1.8 | 17–21 | 21 |
| flc-3 | 22.0 | 5.7 | 27.7 | ±2.1 | 26–31 | 19 |
| Experiment 6 (23°C, long days) | | | | | | |
| Col (wild-type) | 11.9 | 2.9 | 14.8 | ±0.9 | 13–16 | 26 |
| svp-32 | 6.5 | 2.6 | 9.1 | ±0.9 | 8–10 | 25 |
| flm-3 | 10.1 | 2.0 | 12.1 | ±0.9 | 11–13 | 26 |
| tsf-1 | 12.0 | 5.0 | 17.0 | ±2.0 | 15–19 | 24 |
| soc1-2 | 20.6 | 4.5 | 25.1 | ±1.2 | 23–27 | 26 |
| ft-10 | 33.4 | 11.2 | 44.6 | ±3.4 | 41–48 | 25 |
| ft-10 soc1-2 | 49.9 | 10.6 | 60.5 | ±3.6 | 56–65 | 25 |
| ft-10 tsf-1 | 52.4 | 9.6 | 62.0 | ±2.5 | 59–65 | 26 |
| svp-32 ft-10 soc1-2 | 47.6 | 10.6 | 58.2 | ±1.8 | 56–60 | 26 |
| flm-3 ft-10 soc1-2 | 46.7 | 10.7 | 57.4 | ±2.0 | 55–60 | 27 |
| svp-32 ft-10 tsf-1 | 28.1 | 7.9 | 36.0 | ±1.8 | 34–38 | 15 |
| flm-3 ft-10 tsf-1 | 32.1 | 9.9 | 42.0 | ±2.7 | 39–45 | 17 |
| ft-10 soc1-2 tsf-1 | 63.9 | 18.5 | 82.4 | ±6.8 | 75–90 | 8 |
| Experiment 7 (16°C, long days) | | | | | | |
| Col (wild-type) | 22.2 | 5.9 | 28.1 | ±2.4 | 25–31 | 16 |
| svp-32 | 7.0 | 2.4 | 9.4 | ±1.0 | 8–11 | 15 |
| flm-3 | 10.5 | 2.7 | 13.2 | ±0.6 | 12–14 | 17 |
| tsf-1 | 24.0 | 5.7 | 29.7 | ±1.9 | 27–32 | 18 |
| soc1-2 | 39.8 | 7.4 | 47.2 | ±2.7 | 44–50 | 19 |
| ft-10 | 52.3 | 9.8 | 62.1 | ±2.2 | 59–65 | 13 |
| ft-10 soc1-2 | 59.3 | 13.1 | 72.4 | ±4.7 | 67–78 | 12 |
| ft-10 tsf-1 | 64.8 | 15.1 | 79.9 | ±4.6 | 75–85 | 13 |
| svp-32 ft-10 soc1-2 | 59.1 | 11.3 | 70.4 | ±3.2 | 67–74 | 15 |
| flm-3 ft-10 soc1-2 | 58.3 | 9.1 | 67.4 | ±3.7 | 63–72 | 14 |
| svp-32 ft-10 tsf-1 | 35.0 | 10.7 | 45.7 | ±4.7 | 41–51 | 15 |
| flm-3 ft-10 tsf-1 | 41.3 | 14.0 | 55.3 | ±4.6 | 50–60 | 16 |
| ft-10 soc1-2 tsf-1 | 78.1 | 23.3 | 101.4 | ±4.1 | 97–106 | 9 |

Fig. 10a

| Gene | Primer | Purpose | Sequence (5' to 3') | Direction |
|---|---|---|---|---|
| ANNAT1 | JH9547 | qPCR | CGAGAGAGCTATCTTGTTGTGGAC | Sense |
|  | JH9548 | qPCR | TGTCCTTGTGCAAGCAACTTCC | Anti-sense |
| ATDI19 | JH9551 | qPCR | CATCGGGTTGTGCTGTCACATAG | Sense |
|  | JH9552 | qPCR | TAAGAGAACAAACAGGGCATACCG | Anti-sense |
| AT1G13320 | JH6505 | qPCR | GCGGTTGTGGAGAACATGATACG | Sense |
|  | JH6506 |  | GAACCAAACACAATTCGTTGCTG | Anti-sense |
| AT2G28390 | JH7588 | qPCR | TTGATCCACTTGCAGACAAGGC | Sense |
|  | JH7589 |  | TACCCTTTGGCACACCTGATTG | Anti-sense |
| CBF3 | JH7760 | qPCR | TTGAGATGCCGAGTTTGTTGGC | Sense |
|  | JH7761 |  | ATTCCACTGTACGGACGGAAGC | Anti-sense |
| COR15a | JH7758 | qPCR | ACCTCAACGAGGCCACAAAGAAAG | Sense |
|  | JH7759 |  | CGCTTTCTCACCATCTGCTAATGC | Anti-sense |
| FLM | JH6340 | qPCR | TGGTCTAACGGGTGAAAGCAAGTG | Sense |
|  | JH6341 |  | TTCAAGCTTGCTTTGGACTG | Anti-sense |
|  | JH7648 | qPCR | TGTTCAAGCCGGAGAAACCT | Sense |
|  | JH7649 |  | CCATCATCAGTTCTGCCTTCC | Anti-sense |
|  | JH7654 | qPCR | CAGCAAGCTTGAAGAACCAAA | Sense |
|  | JH7655 |  | GCCTAGAATATGGCCTTTATCGAA | Anti-sense |
|  | JH7656 | qPCR | TTGATCGTTATGAAATACAACATGC | Sense |
|  | JH7657 |  | GCAGTCTCAAGTTGTTCCTCCA | Anti-sense |
|  | JH7684 | qPCR | CTATGACTCTTCCTCCGGTGAC | Sense |
|  | JH7685 |  | GTGGAAGATAATTCTGAATTTTTTCTTCAAGAT | Anti-sense |
|  | JH9540 | qPCR | CATGCTGATGAACTTAGAGCCTTAGATC | Sense |
|  | JH9541 | qPCR | CAGCAACGTATTCTTTCCCAT | Anti-sense |
|  | JH9542 | qPCR | GATAGAAGCGCTGTTCAAGC | Sense |
|  | JH4710 | Y2H | catatgATGGGAAGAAGAAAAATCGAGATC | Sense |
|  | JH4711 |  | ggatccATTGAGCAGCGGGAGAGTCTCCGG | Anti-sense |
|  | JH7413 | GVG | CTCGAGATGGGAAGAAGAAAATCGAGATC | Sense |

Fig. 10b

| | | | | |
|---|---|---|---|---|
| | JH7414 | | ACTAGTCTAATTGAGCAGCGGGAGAGTCTC | Anti-sense |
| | JH3280 | Transgene | ctcgagATGGGAAGAAGAAAAATC | Sense |
| | JH3281 | | gacgtcttATTGAGCAGCGGGAGAG | Anti-sense |
| | JH5304 | Localization YFP | actagtATGGGAAGAAGAAAAATCGAGA | Sense |
| | JH5305 | | ctgcagATTGAGCAGCGGGAGAGTC | Anti-sense |
| | JH8967 | GFP | TCTAGAATGGGAAGAAGAAAAATCGAG | Sense |
| | JH8968 | | GGATCCCATTGAGCAGCGGGAGAGTCTC | Anti-sense |
| | JH2275 | Sequencing | TGACAATATTGGCTGCGAAGT | Sense |
| | JH3476 | Sequencing | CGTCTTATGCGTCTTACTAATTGTTCA | Sense |
| | JH3477 | Sequencing | TGAAACTCTGATCATCTGGTGCTCT | Anti-sense |
| | JH7657 | Sequencing | GCAGTCTCAAGTTGTTCCTCCA | Anti-sense |
| FLC | JH3778 | qPCR | GCCAAGAAGACCGAACTCAT | Sense |
| | JH3779 | | TTTGTCCAGCAGGTGACATC | Anti-sense |
| | JH5936 | Y2H | gccatggATGGTCTCATTCTCCG | Sense |
| | JH5937 | | cgtcgacTTGTTCAATCTTTTTCAT | Anti-sense |
| | JH8965 | GFP | TCTAGAATGGGAAGAAAAAACTAGAA | Sense |
| | JH8966 | | GGATCCCATTAAGTAGTGGGAGAGTCAC | Anti-sense |
| FT | JH6488 | qPCR | AGGCCTTCTCAGGTTCAAAACAAGC | Sense |
| | JH6489 | | TGCCAAAGGTTGTTCCAGTTGTAGC | Anti-sense |
| | JH6815 | ChIP-qPCR-I | GGCTATGGTTATAAGTTTCATCTTTGA | Sense |
| | JH6816 | | AATACTAACCATCCATTTGCACGA | Anti-sense |
| | JH6823 | ChIP-qPCR-II | AGTTGAGATTGGTGGAGAAGACCT | Sense |
| | JH6824 | | TGATTTGGGTATCATAAAGTAAAACCA | Anti-sense |
| | JH6829 | ChIP-qPCR-III | TTCAGGTTTTACTCCATCATACGG | Sense |
| | JH6830 | | TGTGATGATGTTTTGGTCAGAGA | Anti-sense |
| SOC1 | JH6165 | qPCR | ATAGGAACATGCTCAATCGAGGAGCTG | Sense |

Fig. 10c

| | | | | |
|---|---|---|---|---|
| | JH6166 | | TTTCTTGAAGAACAAGGTAACCCAATG | Anti-sense |
| | JH6848 | ChIP-qPCR-I | TGGGAGGGAAAAAGATGTGT | Sense |
| | JH6849 | | TGGTAATGGTGTTTGTGAAACC | Anti-sense |
| | JH6853 | ChIP-qPCR-II | CAAATCATCCATAGAAAGAGAGAGA | Sense |
| | JH6854 | | CAAGATGATATACTAGCGGAAATAAAA | Anti-sense |
| | JH6857 | ChIP-qPCR-III | CATGAAAGCGAAGTTTGGTCA | Sense |
| | JH6858 | | GACAACAAGAGAGAAGCAGCTTTAGA | Anti-sense |
| SVP | JH3776 | qPCR | GAAGAGAACGAGCGACTTGG | Sense |
| | JH3777 | | GAGCTCTCGGAGTCAACAGG | Anti-sense |
| | JH4601 | Y2H | gaattcATGGCGAGAGAAAAGATT | Sense |
| | JH2246 | | CTCGAGTCCCTTTTTCTGAAGTTCGCTG | Anti-sense |
| | JH7411 | GVG | ctcgagATGGCGAGAGAAAAGATTCAGATC | Sense |
| | JH7412 | | actagtCTAACCACCATACGGTAAGCCGAG | Anti-sense |
| | JH2934 | Transgene | ggatcccATGGCGAGAGAAAAGATTC | Sense |
| | JH2935 | | ggatccgcACCACCATACGGTAAGCCG | Anti-sense |
| | JH8963 | Localization YFP | tctagaATGGCGAGAGAAAAGATTCAG | Sense |
| | JH8964 | | ggatccCACCACCATACGGTAAGCCGAG | Anti-sense |
| | JH2486 | GST | ggatcctaATGGCGAGAGAAAAGATT | Sense |
| | JH2487 | | ctcgagCTAACCACCATACGGTAAGCC | Anti-sense |
| TSA1 | JH9549 | qPCR | AGCGATTCAACCGCGGACAATAAC | Sense |
| | JH9550 | qPCR | AAGGCTCTCTGTAGCAGCTTCG | Anti-sense |
| TSF | JH6171 | qPCR | CTCGGGAATTCATCGTATTG | Sense |
| | JH6172 | | CCCTCTGGCAGTTGAAGTAA | Anti-sense |
| | JH6444 | ChIP-qPCR-I | CGTCCCACGTATGTTTTCGT | Sense |
| | JH6833 | | TTCCCCAAGTTTGGAAGACAA | Anti-sense |
| | JH6834 | ChIP-qPCR-II | ACTTCTGTTACCTTGTGTCTATTTGTT | Sense |
| | JH6835 | | AAGGACACTACATTACACCGATTA | Anti-sense |

Fig. 10d

|  |  |  | TG | |
| --- | --- | --- | --- | --- |
| | JH6836 | ChIP-qPCR-III | TGATATACGTACGTTGAACGAGTTG | Sense |
| | JH6837 | | GACCACAAGAGGATCTCTACGACTT | Anti-sense |
| | JH6838 | ChIP-qPCR-IV | TTGGAGATGTTCTTGATCCTTTCA | Sense |
| | JH6839 | | ACGAAAGAGTGAGCTACGAGGAAC | Anti-sense |
| | JH6840 | ChIP-qPCR-V | ACGTTTTCAAGAGACGGTTAACTT | Sense |
| | JH6841 | | GAAAAGTGATAACACACATTAAGACGA | Anti-sense |
| | JH6453 | ChIP-qPCR-VI | ACAAAATAGTCTCGCGGTGT | Sense |
| | JH6454 | | TGAAGTATTTAAGCATCTATGTCAATG | Anti-sense |
| VCS | JH9553 | qPCR | TGGCCATTCACAGAGAGTGACG | Sense |
| | JH9554 | qPCR | CCATCTAGGCTAACACTGGCCAAC | Anti-sense |

*Lowercase letters denote synthetic restriction enzyme sites.
†ChIP: chromatin immunoprecipitation.

SEQUENCE LISTING

```
<160> NUMBER OF SEQ ID NOS: 139

<210> SEQ ID NO 1
<211> LENGTH: 21
<212> TYPE: DNA
<213> ORGANISM: Artificial
<220> FEATURE:
<223> OTHER INFORMATION: p35S::amiR-SVP-1

<400> SEQUENCE: 1
ttgtgtaagt ttctgcctat g                                            21

<210> SEQ ID NO 2
<211> LENGTH: 21
<212> TYPE: DNA
<213> ORGANISM: Artificial
<220> FEATURE:
<223> OTHER INFORMATION: p35S::amiR-SVP-2

<400> SEQUENCE: 2
tcgtcggagt ctattactaa c                                            21

<210> SEQ ID NO 3
<211> LENGTH: 21
<212> TYPE: DNA
<213> ORGANISM: Artificial
<220> FEATURE:
<223> OTHER INFORMATION: p35S::amiR-SVP-3
```

-continued

<400> SEQUENCE: 3
cagtgatcac gcccgaatga g                                    21

<210> SEQ ID NO 4
<211> LENGTH: 21
<212> TYPE: DNA
<213> ORGANISM: Artificial
<220> FEATURE:
<223> OTHER INFORMATION: p35S::amiR-FLM-1

<400> SEQUENCE: 4
aagcctgatt cataattaag a                                    21

<210> SEQ ID NO 5
<211> LENGTH: 21
<212> TYPE: DNA
<213> ORGANISM: Artificial
<220> FEATURE:
<223> OTHER INFORMATION: p35S::amiR-FLM-2

<400> SEQUENCE: 5
atgatggagt atatcgagtc c                                    21

<210> SEQ ID NO 6
<211> LENGTH: 21
<212> TYPE: DNA
<213> ORGANISM: Artificial
<220> FEATURE:
<223> OTHER INFORMATION: p35S::amiR-FLM-3

<400> SEQUENCE: 6
ctgctctgtc cgtaagtaga g                                    21

<210> SEQ ID NO 7
<211> LENGTH: 21
<212> TYPE: DNA
<213> ORGANISM: Artificial
<220> FEATURE:
<223> OTHER INFORMATION: SVP-1

<400> SEQUENCE: 7
tataggcaga aacttacaca g                                    21

<210> SEQ ID NO 8
<211> LENGTH: 21
<212> TYPE: DNA
<213> ORGANISM: Artificial
<220> FEATURE:
<223> OTHER INFORMATION: SVP-2

<400> SEQUENCE: 8
ctgtgtaagt ttctgcctat a                                    21

<210> SEQ ID NO 9
<211> LENGTH: 21
<212> TYPE: DNA
<213> ORGANISM: Artificial
<220> FEATURE:
<223> OTHER INFORMATION: SVP-3

<400> SEQUENCE: 9
ctatgtaagt ttcagcctat t                                    21

```
<210> SEQ ID NO 10
<211> LENGTH: 21
<212> TYPE: DNA
<213> ORGANISM: Artificial
<220> FEATURE:
<223> OTHER INFORMATION: SVP-4

<400> SEQUENCE: 10
aataggctga aacttacata g                                        21

<210> SEQ ID NO 11
<211> LENGTH: 21
<212> TYPE: DNA
<213> ORGANISM: Artificial
<220> FEATURE:
<223> OTHER INFORMATION: SVP-5

<400> SEQUENCE: 11
tttagtaata gactccgacg a                                        21

<210> SEQ ID NO 12
<211> LENGTH: 21
<212> TYPE: DNA
<213> ORGANISM: Artificial
<220> FEATURE:
<223> OTHER INFORMATION: SVP-6

<400> SEQUENCE: 12
tcgtcggagt ctattactaa a                                        21

<210> SEQ ID NO 13
<211> LENGTH: 21
<212> TYPE: DNA
<213> ORGANISM: Artificial
<220> FEATURE:
<223> OTHER INFORMATION: SVP-7

<400> SEQUENCE: 13
tcatcggagt ctaatactaa t                                        21

<210> SEQ ID NO 14
<211> LENGTH: 21
<212> TYPE: DNA
<213> ORGANISM: Artificial
<220> FEATURE:
<223> OTHER INFORMATION: SVP-8

<400> SEQUENCE: 14
attagtatta gactccgatg a                                        21

<210> SEQ ID NO 15
<211> LENGTH: 21
<212> TYPE: DNA
<213> ORGANISM: Artificial
<220> FEATURE:
<223> OTHER INFORMATION: SVP-9

<400> SEQUENCE: 15
ttcattcggg cgtgatcact t                                        21

<210> SEQ ID NO 16
<211> LENGTH: 21
<212> TYPE: DNA
<213> ORGANISM: Artificial
<220> FEATURE:
<223> OTHER INFORMATION: SVP-10
```

<400> SEQUENCE: 16
aagtgatcac gcccgaatga a       21

<210> SEQ ID NO 17
<211> LENGTH: 21
<212> TYPE: DNA
<213> ORGANISM: Artificial
<220> FEATURE:
<223> OTHER INFORMATION: SVP-11

<400> SEQUENCE: 17
aaatgatcac gccggaatga t       21

<210> SEQ ID NO 18
<211> LENGTH: 21
<212> TYPE: DNA
<213> ORGANISM: Artificial
<220> FEATURE:
<223> OTHER INFORMATION: SVP-12

<400> SEQUENCE: 18
atcattccgg cgtgatcatt t       21

<210> SEQ ID NO 19
<211> LENGTH: 21
<212> TYPE: DNA
<213> ORGANISM: Artificial
<220> FEATURE:
<223> OTHER INFORMATION: FLM-1

<400> SEQUENCE: 19
tcttaattat gaatcaggcg t       21

<210> SEQ ID NO 20
<211> LENGTH: 21
<212> TYPE: DNA
<213> ORGANISM: Artificial
<220> FEATURE:
<223> OTHER INFORMATION: FLM-2

<400> SEQUENCE: 20
acgcctgatt cataattaag a       21

<210> SEQ ID NO 21
<211> LENGTH: 21
<212> TYPE: DNA
<213> ORGANISM: Artificial
<220> FEATURE:
<223> OTHER INFORMATION: FLM-3

<400> SEQUENCE: 21
acacctgatt cattattaag t       21

<210> SEQ ID NO 22
<211> LENGTH: 21
<212> TYPE: DNA
<213> ORGANISM: Artificial
<220> FEATURE:
<223> OTHER INFORMATION: FLM-4

<400> SEQUENCE: 22
acttaataat gaatcaggtg t       21

```
<210> SEQ ID NO 23
<211> LENGTH: 21
<212> TYPE: DNA
<213> ORGANISM: Artificial
<220> FEATURE:
<223> OTHER INFORMATION: FLM-5

<400> SEQUENCE: 23
tgactcgata tactgcgtca t                                              21

<210> SEQ ID NO 24
<211> LENGTH: 21
<212> TYPE: DNA
<213> ORGANISM: Artificial
<220> FEATURE:
<223> OTHER INFORMATION: FLM-6

<400> SEQUENCE: 24
atgacgcagt atatcgagtc a                                              21

<210> SEQ ID NO 25
<211> LENGTH: 21
<212> TYPE: DNA
<213> ORGANISM: Artificial
<220> FEATURE:
<223> OTHER INFORMATION: FLM-7

<400> SEQUENCE: 25
ataacgcagt ataacgagtc t                                              21

<210> SEQ ID NO 26
<211> LENGTH: 21
<212> TYPE: DNA
<213> ORGANISM: Artificial
<220> FEATURE:
<223> OTHER INFORMATION: FLM-8

<400> SEQUENCE: 26
agactcgtta tactgcgtta t                                              21

<210> SEQ ID NO 27
<211> LENGTH: 21
<212> TYPE: DNA
<213> ORGANISM: Artificial
<220> FEATURE:
<223> OTHER INFORMATION: FLM-9

<400> SEQUENCE: 27
ttctacttac ggatagcgca g                                              21

<210> SEQ ID NO 28
<211> LENGTH: 21
<212> TYPE: DNA
<213> ORGANISM: Artificial
<220> FEATURE:
<223> OTHER INFORMATION: FLM-10

<400> SEQUENCE: 28
ctgcgctatc cgtaagtaga a                                              21

<210> SEQ ID NO 29
<211> LENGTH: 21
<212> TYPE: DNA
<213> ORGANISM: Artificial
<220> FEATURE:
<223> OTHER INFORMATION: FLM-11
```

```
<400> SEQUENCE: 29
ctacgctatc cgttagtaga t                                              21

<210> SEQ ID NO 30
<211> LENGTH: 21
<212> TYPE: DNA
<213> ORGANISM: Artificial
<220> FEATURE:
<223> OTHER INFORMATION: FLM-12

<400> SEQUENCE: 30
atctactaac ggatagcgta g                                              21

<210> SEQ ID NO 31
<211> LENGTH: 21
<212> TYPE: DNA
<213> ORGANISM: Artificial
<220> FEATURE:
<223> OTHER INFORMATION: SVP31

<400> SEQUENCE: 31
ctgcatttct ggttagtaac g                                              21

<210> SEQ ID NO 32
<211> LENGTH: 21
<212> TYPE: DNA
<213> ORGANISM: Artificial
<220> FEATURE:
<223> OTHER INFORMATION: SVP32

<400> SEQUENCE: 32
acgcttgtca ccgataaact t                                              21

<210> SEQ ID NO 33
<211> LENGTH: 21
<212> TYPE: DNA
<213> ORGANISM: Artificial
<220> FEATURE:
<223> OTHER INFORMATION: SVP33

<400> SEQUENCE: 33
aagagacaat gtctaagtag t                                              21

<210> SEQ ID NO 34
<211> LENGTH: 21
<212> TYPE: DNA
<213> ORGANISM: Artificial
<220> FEATURE:
<223> OTHER INFORMATION: SVP34

<400> SEQUENCE: 34
taggctcggc ttaccgtatg g                                              21

<210> SEQ ID NO 35
<211> LENGTH: 21
<212> TYPE: DNA
<213> ORGANISM: Artificial
<220> FEATURE:
<223> OTHER INFORMATION: SVP35

<400> SEQUENCE: 35
aagtcctaga gaggcataac t                                              21
```

```
<210> SEQ ID NO 36
<211> LENGTH: 21
<212> TYPE: DNA
<213> ORGANISM: Artificial
<220> FEATURE:
<223> OTHER INFORMATION: SVP36

<400> SEQUENCE: 36
gagcgacttg gcatgcaaat a                                              21

<210> SEQ ID NO 37
<211> LENGTH: 21
<212> TYPE: DNA
<213> ORGANISM: Artificial
<220> FEATURE:
<223> OTHER INFORMATION: SVP37

<400> SEQUENCE: 37
cagcaaggaa cgcaactaac g                                              21

<210> SEQ ID NO 38
<211> LENGTH: 21
<212> TYPE: DNA
<213> ORGANISM: Artificial
<220> FEATURE:
<223> OTHER INFORMATION: SVP38

<400> SEQUENCE: 38
tcggcttacc gtatggtggt t                                              21

<210> SEQ ID NO 39
<211> LENGTH: 21
<212> TYPE: DNA
<213> ORGANISM: Artificial
<220> FEATURE:
<223> OTHER INFORMATION: SVP39

<400> SEQUENCE: 39
tcggagaacg ctgctgtgta c                                              21

<210> SEQ ID NO 40
<211> LENGTH: 21
<212> TYPE: DNA
<213> ORGANISM: Artificial
<220> FEATURE:
<223> OTHER INFORMATION: FLM40

<400> SEQUENCE: 40
gagtatatcg agtcccttaa a                                              21

<210> SEQ ID NO 41
<211> LENGTH: 21
<212> TYPE: DNA
<213> ORGANISM: Artificial
<220> FEATURE:
<223> OTHER INFORMATION: FLM41

<400> SEQUENCE: 41
aagctcgaca actttcgatt c                                              21

<210> SEQ ID NO 42
<211> LENGTH: 21
<212> TYPE: DNA
<213> ORGANISM: Artificial
<220> FEATURE:
<223> OTHER INFORMATION: FLM42
```

<400> SEQUENCE: 42
gtgtctgaat gtacggattg g 21

<210> SEQ ID NO 43
<211> LENGTH: 21
<212> TYPE: DNA
<213> ORGANISM: Artificial
<220> FEATURE:
<223> OTHER INFORMATION: FLM43

<400> SEQUENCE: 43
atgggaaaga atacgttgct g 21

<210> SEQ ID NO 44
<211> LENGTH: 21
<212> TYPE: DNA
<213> ORGANISM: Artificial
<220> FEATURE:
<223> OTHER INFORMATION: FLM44

<400> SEQUENCE: 44
tagggcataa cccttatcgg a 21

<210> SEQ ID NO 45
<211> LENGTH: 21
<212> TYPE: DNA
<213> ORGANISM: Artificial
<220> FEATURE:
<223> OTHER INFORMATION: FLM45

<400> SEQUENCE: 45
ttgtgtctga atgtacggat t 21

<210> SEQ ID NO 46
<211> LENGTH: 21
<212> TYPE: DNA
<213> ORGANISM: Artificial
<220> FEATURE:
<223> OTHER INFORMATION: FLM46

<400> SEQUENCE: 46
ttgtacctcc ttcggagaca a 21

<210> SEQ ID NO 47
<211> LENGTH: 21
<212> TYPE: DNA
<213> ORGANISM: Artificial
<220> FEATURE:
<223> OTHER INFORMATION: FLM47

<400> SEQUENCE: 47
acggctgagt tttcacctta a 21

<210> SEQ ID NO 48
<211> LENGTH: 21
<212> TYPE: DNA
<213> ORGANISM: Artificial
<220> FEATURE:
<223> OTHER INFORMATION: FLM48

<400> SEQUENCE: 48
gagctaggaa ggcagaactg a 21

<210> SEQ ID NO 49
<211> LENGTH: 24
<212> TYPE: DNA
<213> ORGANISM: Artificial
<220> FEATURE:
<223> OTHER INFORMATION: JH9547

<400> SEQUENCE: 49
cgagagagct atcttgttgt ggac                                       24

<210> SEQ ID NO 50
<211> LENGTH: 22
<212> TYPE: DNA
<213> ORGANISM: Artificial
<220> FEATURE:
<223> OTHER INFORMATION: JH9548

<400> SEQUENCE: 50
tgtccttgtg caagcaactt cc                                         22

<210> SEQ ID NO 51
<211> LENGTH: 23
<212> TYPE: DNA
<213> ORGANISM: Artificial
<220> FEATURE:
<223> OTHER INFORMATION: JH9551

<400> SEQUENCE: 51
catcgggttg tgctgtcaca tag                                        23

<210> SEQ ID NO 52
<211> LENGTH: 24
<212> TYPE: DNA
<213> ORGANISM: Artificial
<220> FEATURE:
<223> OTHER INFORMATION: JH9552

<400> SEQUENCE: 52
taagagaaca aacagggcat accg                                       24

<210> SEQ ID NO 53
<211> LENGTH: 23
<212> TYPE: DNA
<213> ORGANISM: Artificial
<220> FEATURE:
<223> OTHER INFORMATION: JH6505

<400> SEQUENCE: 53
gcggttgtgg agaacatgat acg                                        23

<210> SEQ ID NO 54
<211> LENGTH: 23
<212> TYPE: DNA
<213> ORGANISM: Artificial
<220> FEATURE:
<223> OTHER INFORMATION: JH6506

<400> SEQUENCE: 54
gaaccaaaca caattcgttg ctg                                        23

<210> SEQ ID NO 55
<211> LENGTH: 22
<212> TYPE: DNA
<213> ORGANISM: Artificial
<220> FEATURE:
<223> OTHER INFORMATION: JH7588

-continued

<400> SEQUENCE: 55
ttgatccact tgcagacaag gc                                          22

<210> SEQ ID NO 56
<211> LENGTH: 22
<212> TYPE: DNA
<213> ORGANISM: Artificial
<220> FEATURE:
<223> OTHER INFORMATION: JH7589

<400> SEQUENCE: 56 tacccttttgg cacacctgat tg                                         22

<210> SEQ ID NO 57
<211> LENGTH: 22
<212> TYPE: DNA
<213> ORGANISM: Artificial
<220> FEATURE:
<223> OTHER INFORMATION: JH7760

<400> SEQUENCE: 57
ttgagatgcc gagtttgttg gc                                          22

<210> SEQ ID NO 58
<211> LENGTH: 22
<212> TYPE: DNA
<213> ORGANISM: Artificial
<220> FEATURE:
<223> OTHER INFORMATION: JH7761

<400> SEQUENCE: 58
attccactgt acggacggaa gc                                          22

<210> SEQ ID NO 59
<211> LENGTH: 24
<212> TYPE: DNA
<213> ORGANISM: Artificial
<220> FEATURE:
<223> OTHER INFORMATION: JH7758

<400> SEQUENCE: 59
acctcaacga ggccacaaag aaag                                        24

<210> SEQ ID NO 60
<211> LENGTH: 24
<212> TYPE: DNA
<213> ORGANISM: Artificial
<220> FEATURE:
<223> OTHER INFORMATION: JH7759

<400> SEQUENCE: 60
cgctttctca ccatctgcta atgc                                        24

<210> SEQ ID NO 61
<211> LENGTH: 24
<212> TYPE: DNA
<213> ORGANISM: Artificial
<220> FEATURE:
<223> OTHER INFORMATION: JH6340

<400> SEQUENCE: 61
tggtctaacg ggtgaaagca agtg                                        24

```
<210> SEQ ID NO 62
<211> LENGTH: 20
<212> TYPE: DNA
<213> ORGANISM: Artificial
<220> FEATURE:
<223> OTHER INFORMATION: JH6341

<400> SEQUENCE: 62
ttcaagcttg ctttggactg                                            20

<210> SEQ ID NO 63
<211> LENGTH: 20
<212> TYPE: DNA
<213> ORGANISM: Artificial
<220> FEATURE:
<223> OTHER INFORMATION: JH7648

<400> SEQUENCE: 63
tgttcaagcc ggagaaacct                                            20

<210> SEQ ID NO 64
<211> LENGTH: 21
<212> TYPE: DNA
<213> ORGANISM: Artificial
<220> FEATURE:
<223> OTHER INFORMATION: JH7649

<400> SEQUENCE: 64
ccatcatcag ttctgccttc c                                          21

<210> SEQ ID NO 65
<211> LENGTH: 21
<212> TYPE: DNA
<213> ORGANISM: Artificial
<220> FEATURE:
<223> OTHER INFORMATION: JH7654

<400> SEQUENCE: 65
cagcaagctt gaagaaccaa a                                          21

<210> SEQ ID NO 66
<211> LENGTH: 24
<212> TYPE: DNA
<213> ORGANISM: Artificial
<220> FEATURE:
<223> OTHER INFORMATION: JH7655

<400> SEQUENCE: 66
gcctagaata tggcctttat cgaa                                       24

<210> SEQ ID NO 67
<211> LENGTH: 25
<212> TYPE: DNA
<213> ORGANISM: Artificial
<220> FEATURE:
<223> OTHER INFORMATION: JH7656

<400> SEQUENCE: 67
ttgatcgtta tgaaatacaa catgc                                      25

<210> SEQ ID NO 68
<211> LENGTH: 22
<212> TYPE: DNA
<213> ORGANISM: Artificial
<220> FEATURE:
<223> OTHER INFORMATION: JH7657
```

```
<400> SEQUENCE: 68
gcagtctcaa gttgttcctc ca                                              22

<210> SEQ ID NO 69
<211> LENGTH: 22
<212> TYPE: DNA
<213> ORGANISM: Artificial
<220> FEATURE:
<223> OTHER INFORMATION: JH7684

<400> SEQUENCE: 69
ctatgactct tcctccggtg ac                                              22

<210> SEQ ID NO 70
<211> LENGTH: 33
<212> TYPE: DNA
<213> ORGANISM: Artificial
<220> FEATURE:
<223> OTHER INFORMATION: JH7685

<400> SEQUENCE: 70
gtggaagata attctgaatt ttttcttcaa gat                                  33

<210> SEQ ID NO 71
<211> LENGTH: 28
<212> TYPE: DNA
<213> ORGANISM: Artificial
<220> FEATURE:
<223> OTHER INFORMATION: JH9540

<400> SEQUENCE: 71
catgctgatg aacttagagc cttagatc                                        28

<210> SEQ ID NO 72
<211> LENGTH: 21
<212> TYPE: DNA
<213> ORGANISM: Artificial
<220> FEATURE:
<223> OTHER INFORMATION: JH9541

<400> SEQUENCE: 72
cagcaacgta ttctttccca t                                               21

<210> SEQ ID NO 73
<211> LENGTH: 20
<212> TYPE: DNA
<213> ORGANISM: Artificial
<220> FEATURE:
<223> OTHER INFORMATION: JH9542

<400> SEQUENCE: 73
gatagaagcg ctgttcaagc                                                 20

<210> SEQ ID NO 74
<211> LENGTH: 30
<212> TYPE: DNA
<213> ORGANISM: Artificial
<220> FEATURE:
<223> OTHER INFORMATION: JH4710

<400> SEQUENCE: 74
catatgatgg gaagaagaaa aatcgagatc                                      30
```

<210> SEQ ID NO 75
<211> LENGTH: 30
<212> TYPE: DNA
<213> ORGANISM: Artificial
<220> FEATURE:
<223> OTHER INFORMATION: JH4711

<400> SEQUENCE: 75
ggatccattg agcagcggga gagtctccgg                               30

<210> SEQ ID NO 76
<211> LENGTH: 30
<212> TYPE: DNA
<213> ORGANISM: Artificial
<220> FEATURE:
<223> OTHER INFORMATION: JH7413

<400> SEQUENCE: 76
ctcgagatgg gaagaagaaa aatcgagatc                               30

<210> SEQ ID NO 77
<211> LENGTH: 30
<212> TYPE: DNA
<213> ORGANISM: Artificial
<220> FEATURE:
<223> OTHER INFORMATION: JH7414

<400> SEQUENCE: 77
actagtctaa ttgagcagcg ggagagtctc                               30

<210> SEQ ID NO 78
<211> LENGTH: 24
<212> TYPE: DNA
<213> ORGANISM: Artificial
<220> FEATURE:
<223> OTHER INFORMATION: JH3280

<400> SEQUENCE: 78
ctcgagatgg gaagaagaaa aatc                                     24

<210> SEQ ID NO 79
<211> LENGTH: 25
<212> TYPE: DNA
<213> ORGANISM: Artificial
<220> FEATURE:
<223> OTHER INFORMATION: JH3281

<400> SEQUENCE: 79
gacgtcttat tgagcagcgg gagag                                    25

<210> SEQ ID NO 80
<211> LENGTH: 28
<212> TYPE: DNA
<213> ORGANISM: Artificial
<220> FEATURE:
<223> OTHER INFORMATION: JH5304

<400> SEQUENCE: 80
actagtatgg gaagaagaaa aatcgaga                                 28

<210> SEQ ID NO 81
<211> LENGTH: 25
<212> TYPE: DNA
<213> ORGANISM: Artificial
<220> FEATURE:
<223> OTHER INFORMATION: JH5305

```
<400> SEQUENCE: 81
ctgcagattg agcagcggga gagtc                                           25

<210> SEQ ID NO 82
<211> LENGTH: 27
<212> TYPE: DNA
<213> ORGANISM: Artificial
<220> FEATURE:
<223> OTHER INFORMATION: JH8967

<400> SEQUENCE: 82
tctagaatgg gaagaagaaa aatcgag                                         27

<210> SEQ ID NO 83
<211> LENGTH: 28
<212> TYPE: DNA
<213> ORGANISM: Artificial
<220> FEATURE:
<223> OTHER INFORMATION: JH8968

<400> SEQUENCE: 83
ggatcccatt gagcagcggg agagtctc                                        28

<210> SEQ ID NO 84
<211> LENGTH: 21
<212> TYPE: DNA
<213> ORGANISM: Artificial
<220> FEATURE:
<223> OTHER INFORMATION: JH2275

<400> SEQUENCE: 84
tgacaatatt ggctgcgaag t                                               21

<210> SEQ ID NO 85
<211> LENGTH: 27
<212> TYPE: DNA
<213> ORGANISM: Artificial
<220> FEATURE:
<223> OTHER INFORMATION: JH3476

<400> SEQUENCE: 85
cgtcttatgc gtcttactaa ttgttca                                         27

<210> SEQ ID NO 86
<211> LENGTH: 25
<212> TYPE: DNA
<213> ORGANISM: Artificial
<220> FEATURE:
<223> OTHER INFORMATION: JH3477

<400> SEQUENCE: 86
tgaaactctg atcatctggt gctct                                           25

<210> SEQ ID NO 87
<211> LENGTH: 22
<212> TYPE: DNA
<213> ORGANISM: Artificial
<220> FEATURE:
<223> OTHER INFORMATION: JH7657

<400> SEQUENCE: 87
gcagtctcaa gttgttcctc ca                                              22
```

```
<210> SEQ ID NO 88
<211> LENGTH: 20
<212> TYPE: DNA
<213> ORGANISM: Artificial
<220> FEATURE:
<223> OTHER INFORMATION: JH3778

<400> SEQUENCE: 88
gccaagaaga ccgaactcat                                              20

<210> SEQ ID NO 89
<211> LENGTH: 20
<212> TYPE: DNA
<213> ORGANISM: Artificial
<220> FEATURE:
<223> OTHER INFORMATION: JH3779

<400> SEQUENCE: 89
tttgtccagc aggtgacatc                                              20

<210> SEQ ID NO 90
<211> LENGTH: 23
<212> TYPE: DNA
<213> ORGANISM: Artificial
<220> FEATURE:
<223> OTHER INFORMATION: JH5936

<400> SEQUENCE: 90
gccatggatg gtctcattct ccg                                          23

<210> SEQ ID NO 91
<211> LENGTH: 25
<212> TYPE: DNA
<213> ORGANISM: Artificial
<220> FEATURE:
<223> OTHER INFORMATION: JH5937

<400> SEQUENCE: 91
cgtcgacttg ttcaatcttt ttcat                                        25

<210> SEQ ID NO 92
<211> LENGTH: 27
<212> TYPE: DNA
<213> ORGANISM: Artificial
<220> FEATURE:
<223> OTHER INFORMATION: JH8965

<400> SEQUENCE: 92
tctagaatgg gaagaaaaaa actagaa                                      27

<210> SEQ ID NO 93
<211> LENGTH: 28
<212> TYPE: DNA
<213> ORGANISM: Artificial
<220> FEATURE:
<223> OTHER INFORMATION: JH8966

<400> SEQUENCE: 93
ggatcccatt aagtagtggg agagtcac                                     28

<210> SEQ ID NO 94
<211> LENGTH: 25
<212> TYPE: DNA
<213> ORGANISM: Artificial
<220> FEATURE:
<223> OTHER INFORMATION: JH6488
```

```
<400> SEQUENCE: 94
aggccttctc aggttcaaaa caagc                                           25

<210> SEQ ID NO 95
<211> LENGTH: 25
<212> TYPE: DNA
<213> ORGANISM: Artificial
<220> FEATURE:
<223> OTHER INFORMATION: JH6489

<400> SEQUENCE: 95
tgccaaaggt tgttccagtt gtagc                                           25

<210> SEQ ID NO 96
<211> LENGTH: 27
<212> TYPE: DNA
<213> ORGANISM: Artificial
<220> FEATURE:
<223> OTHER INFORMATION: JH6815

<400> SEQUENCE: 96
ggctatggtt ataagtttca tctttga                                         27

<210> SEQ ID NO 97
<211> LENGTH: 24
<212> TYPE: DNA
<213> ORGANISM: Artificial
<220> FEATURE:
<223> OTHER INFORMATION: JH6816

<400> SEQUENCE: 97
aatactaacc atccatttgc acga                                            24

<210> SEQ ID NO 98
<211> LENGTH: 24
<212> TYPE: DNA
<213> ORGANISM: Artificial
<220> FEATURE:
<223> OTHER INFORMATION: JH6823

<400> SEQUENCE: 98
agttgagatt ggtggagaag acct                                            24

<210> SEQ ID NO 99
<211> LENGTH: 27
<212> TYPE: DNA
<213> ORGANISM: Artificial
<220> FEATURE:
<223> OTHER INFORMATION: JH6824

<400> SEQUENCE: 99
tgatttgggt atcataaagt aaaacca                                         27

<210> SEQ ID NO 100
<211> LENGTH: 24
<212> TYPE: DNA
<213> ORGANISM: Artificial
<220> FEATURE:
<223> OTHER INFORMATION: JH6829

<400> SEQUENCE: 100
ttcaggtttt actccatcat acgg                                            24
```

```
<210> SEQ ID NO 101
<211> LENGTH: 24
<212> TYPE: DNA
<213> ORGANISM: Artificial
<220> FEATURE:
<223> OTHER INFORMATION: JH6830

<400> SEQUENCE: 101
tgtgatgatg tttttggtca gaga                                          24

<210> SEQ ID NO 102
<211> LENGTH: 27
<212> TYPE: DNA
<213> ORGANISM: Artificial
<220> FEATURE:
<223> OTHER INFORMATION: JH6165

<400> SEQUENCE: 102
ataggaacat gctcaatcga ggagctg                                       27

<210> SEQ ID NO 103
<211> LENGTH: 27
<212> TYPE: DNA
<213> ORGANISM: Artificial
<220> FEATURE:
<223> OTHER INFORMATION: JH6166

<400> SEQUENCE: 103
tttcttgaag aacaaggtaa cccaatg                                       27

<210> SEQ ID NO 104
<211> LENGTH: 20
<212> TYPE: DNA
<213> ORGANISM: Artificial
<220> FEATURE:
<223> OTHER INFORMATION: JH6848

<400> SEQUENCE: 104
tgggagggaa aaagatgtgt                                               20

<210> SEQ ID NO 105
<211> LENGTH: 22
<212> TYPE: DNA
<213> ORGANISM: Artificial
<220> FEATURE:
<223> OTHER INFORMATION: JH6849

<400> SEQUENCE: 105
tggtaatggt gtttgtgaaa cc                                            22

<210> SEQ ID NO 106
<211> LENGTH: 27
<212> TYPE: DNA
<213> ORGANISM: Artificial
<220> FEATURE:
<223> OTHER INFORMATION: JH6853

<400> SEQUENCE: 106
caaatcatcc atagaaagag agagaga                                       27

<210> SEQ ID NO 107
<211> LENGTH: 27
<212> TYPE: DNA
<213> ORGANISM: Artificial
<220> FEATURE:
<223> OTHER INFORMATION: JH6854
```

<400> SEQUENCE: 107
caagatgata tactagcgga aataaaa                                              27

<210> SEQ ID NO 108
<211> LENGTH: 21
<212> TYPE: DNA
<213> ORGANISM: Artificial
<220> FEATURE:
<223> OTHER INFORMATION: JH6857

<400> SEQUENCE: 108
catgaaagcg aagtttggtc a                                                    21

<210> SEQ ID NO 109
<211> LENGTH: 26
<212> TYPE: DNA
<213> ORGANISM: Artificial
<220> FEATURE:
<223> OTHER INFORMATION: JH6858

<400> SEQUENCE: 109
gacaacaaga gagaagcagc tttaga                                               26

<210> SEQ ID NO 110
<211> LENGTH: 20
<212> TYPE: DNA
<213> ORGANISM: Artificial
<220> FEATURE:
<223> OTHER INFORMATION: JH3776

<400> SEQUENCE: 110
gaagagaacg agcgacttgg                                                      20

<210> SEQ ID NO 111
<211> LENGTH: 20
<212> TYPE: DNA
<213> ORGANISM: Artificial
<220> FEATURE:
<223> OTHER INFORMATION: JH3777

<400> SEQUENCE: 111
gagctctcgg agtcaacagg                                                      20

<210> SEQ ID NO 112
<211> LENGTH: 24
<212> TYPE: DNA
<213> ORGANISM: Artificial
<220> FEATURE:
<223> OTHER INFORMATION: JH4601

<400> SEQUENCE: 112
gaattcatgg cgagagaaaa gatt                                                 24

<210> SEQ ID NO 113
<211> LENGTH: 28
<212> TYPE: DNA
<213> ORGANISM: Artificial
<220> FEATURE:
<223> OTHER INFORMATION: JH2246

<400> SEQUENCE: 113
ctcgagtccc ttttctgaa gttcgctg                                              28

```
<210> SEQ ID NO 114
<211> LENGTH: 30
<212> TYPE: DNA
<213> ORGANISM: Artificial
<220> FEATURE:
<223> OTHER INFORMATION: JH7411

<400> SEQUENCE: 114
ctcgagatgg cgagagaaaa gattcagatc                                    30

<210> SEQ ID NO 115
<211> LENGTH: 30
<212> TYPE: DNA
<213> ORGANISM: Artificial
<220> FEATURE:
<223> OTHER INFORMATION: JH7412

<400> SEQUENCE: 115
actagtctaa ccaccatacg gtaagccgag                                    30

<210> SEQ ID NO 116
<211> LENGTH: 26
<212> TYPE: DNA
<213> ORGANISM: Artificial
<220> FEATURE:
<223> OTHER INFORMATION: JH2934

<400> SEQUENCE: 116
ggatcccatg gcgagagaaa agattc                                        26

<210> SEQ ID NO 117
<211> LENGTH: 27
<212> TYPE: DNA
<213> ORGANISM: Artificial
<220> FEATURE:
<223> OTHER INFORMATION: JH2935

<400> SEQUENCE: 117
ggatccgcac caccatacgg taagccg                                       27

<210> SEQ ID NO 118
<211> LENGTH: 27
<212> TYPE: DNA
<213> ORGANISM: Artificial
<220> FEATURE:
<223> OTHER INFORMATION: JH8963

<400> SEQUENCE: 118
tctagaatgg cgagagaaaa gattcag                                       27

<210> SEQ ID NO 119
<211> LENGTH: 28
<212> TYPE: DNA
<213> ORGANISM: Artificial
<220> FEATURE:
<223> OTHER INFORMATION: JH8964

<400> SEQUENCE: 119
ggatcccacc accatacggt aagccgag                                      28

<210> SEQ ID NO 120
<211> LENGTH: 26
<212> TYPE: DNA
<213> ORGANISM: Artificial
<220> FEATURE:
<223> OTHER INFORMATION: JH2486
```

```
<400> SEQUENCE: 120
ggatcctaat ggcgagagaa aagatt                                          26

<210> SEQ ID NO 121
<211> LENGTH: 27
<212> TYPE: DNA
<213> ORGANISM: Artificial
<220> FEATURE:
<223> OTHER INFORMATION: JH2487

<400> SEQUENCE: 121
ctcgagctaa ccaccatacg gtaagcc                                         27

<210> SEQ ID NO 122
<211> LENGTH: 24
<212> TYPE: DNA
<213> ORGANISM: Artificial
<220> FEATURE:
<223> OTHER INFORMATION: JH9549

<400> SEQUENCE: 122
agcgattcaa ccgcggacaa taac                                            24

<210> SEQ ID NO 123
<211> LENGTH: 22
<212> TYPE: DNA
<213> ORGANISM: Artificial
<220> FEATURE:
<223> OTHER INFORMATION: JH9550

<400> SEQUENCE: 123
aaggctctct gtagcagctt cg                                              22

<210> SEQ ID NO 124
<211> LENGTH: 20
<212> TYPE: DNA
<213> ORGANISM: Artificial
<220> FEATURE:
<223> OTHER INFORMATION: JH6171

<400> SEQUENCE: 124
ctcgggaatt catcgtattg                                                 20

<210> SEQ ID NO 125
<211> LENGTH: 20
<212> TYPE: DNA
<213> ORGANISM: Artificial
<220> FEATURE:
<223> OTHER INFORMATION: JH6172

<400> SEQUENCE: 125
ccctctggca gttgaagtaa                                                 20

<210> SEQ ID NO 126
<211> LENGTH: 20
<212> TYPE: DNA
<213> ORGANISM: Artificial
<220> FEATURE:
<223> OTHER INFORMATION: JH6444

<400> SEQUENCE: 126
cgtcccacgt atgttttcgt                                                 20
```

<210> SEQ ID NO 127
<211> LENGTH: 21
<212> TYPE: DNA
<213> ORGANISM: Artificial
<220> FEATURE:
<223> OTHER INFORMATION: JH6833

<400> SEQUENCE: 127
ttccccaagt ttggaagaca a                                    21

<210> SEQ ID NO 128
<211> LENGTH: 27
<212> TYPE: DNA
<213> ORGANISM: Artificial
<220> FEATURE:
<223> OTHER INFORMATION: JH6834

<400> SEQUENCE: 128
acttctgtta ccttgtgtct atttgtt                              27

<210> SEQ ID NO 129
<211> LENGTH: 26
<212> TYPE: DNA
<213> ORGANISM: Artificial
<220> FEATURE:
<223> OTHER INFORMATION: JH6835

<400> SEQUENCE: 129
aaggacacta cattacaccg attatg                               26

<210> SEQ ID NO 130
<211> LENGTH: 25
<212> TYPE: DNA
<213> ORGANISM: Artificial
<220> FEATURE:
<223> OTHER INFORMATION: JH6836

<400> SEQUENCE: 130
tgatatacgt acgttgaacg agttg                                25

<210> SEQ ID NO 131
<211> LENGTH: 25
<212> TYPE: DNA
<213> ORGANISM: Artificial
<220> FEATURE:
<223> OTHER INFORMATION: JH6837

<400> SEQUENCE: 131
gaccacaaga ggatctctac gactt                                25

<210> SEQ ID NO 132
<211> LENGTH: 24
<212> TYPE: DNA
<213> ORGANISM: Artificial
<220> FEATURE:
<223> OTHER INFORMATION: JH6838

<400> SEQUENCE: 132
ttggagatgt tcttgatcct ttca                                 24

<210> SEQ ID NO 133
<211> LENGTH: 24
<212> TYPE: DNA
<213> ORGANISM: Artificial
<220> FEATURE:
<223> OTHER INFORMATION: JH6839

<400> SEQUENCE: 133
acgaaagagt gagctacgag gaac        24

<210> SEQ ID NO 134
<211> LENGTH: 24
<212> TYPE: DNA
<213> ORGANISM: Artificial
<220> FEATURE:
<223> OTHER INFORMATION: JH6840

<400> SEQUENCE: 134
acgttttcaa gagacggtta actt        24

<210> SEQ ID NO 135
<211> LENGTH: 27
<212> TYPE: DNA
<213> ORGANISM: Artificial
<220> FEATURE:
<223> OTHER INFORMATION: JH6841

<400> SEQUENCE: 135
gaaaagtgat aacacacatt aagacga     27

<210> SEQ ID NO 136
<211> LENGTH: 20
<212> TYPE: DNA
<213> ORGANISM: Artificial
<220> FEATURE:
<223> OTHER INFORMATION: JH6453

<400> SEQUENCE: 136
acaaaatagt ctcgcggtgt             20

<210> SEQ ID NO 137
<211> LENGTH: 27
<212> TYPE: DNA
<213> ORGANISM: Artificial
<220> FEATURE:
<223> OTHER INFORMATION: JH6454

<400> SEQUENCE: 137
tgaagtattt aagcatctat gtcaatg     27

<210> SEQ ID NO 138
<211> LENGTH: 22
<212> TYPE: DNA
<213> ORGANISM: Artificial
<220> FEATURE:
<223> OTHER INFORMATION: JH9553

<400> SEQUENCE: 138
tggccattca cagagagtga cg          22

<210> SEQ ID NO 139
<211> LENGTH: 24
<212> TYPE: DNA
<213> ORGANISM: Artificial
<220> FEATURE:
<223> OTHER INFORMATION: JH9554

<400> SEQUENCE: 139
ccatctaggc taacactggc caac        24

METHOD FOR CONTROLLING FLOWERING TIME BY REGULATING OF SVP-FLM-β PROTEIN COMPLEX FORMATION

CROSS-REFERENCE TO RELATED APPLICATION

This application claims priority under the provisions of 35 U.S.C. § 119 of Korean Patent Application No. 10-2014-0005283 filed Jan. 15, 2014. The disclosure of such Korean patent application is hereby incorporated herein by reference in its entirety, for all purposes.

TECHNICAL FIELD

The present invention relates to a method of controlling the flowering time of a plant by regulating the formation of the SVP-FLM-β protein complex, based on the finding that the SVP-FLM-β protein complex is a regulating factor for plant flowering that senses small changes in ambient temperature.

BACKGROUND ART

RNA interference (RNAi) is a mechanism capable of inhibiting the expression of a gene in a highly specific and efficient manner, in which degradation of the mRNA of a target gene is inhibited by introducing a double-stranded RNA, which comprises a sense strand having a sequence homologous to the mRNA of the target gene and an antisense strand having a sequence complementary to the sense strand, into cells or the like, thereby inhibiting the expression of the target gene. Since it was known that low-molecular-weight RNA (non-coding RNA) that is not translated in *C. elegans* controls the expression of genes in the developmental stage, it was found that many low-molecular-weight RNAs are present in the *C. elegans* genome (Fire et al., *Nature* 391:806-811, 1998). Such low-molecular-weight RNAs have a size of about 25 nucleotides (nt) or shorter and are also called micro RNA (miRNA), and about 200 or more types of miRNAs are present in *C. elegans*. miRNA was also found in plants, and among low-molecular-weight RNAs (21 to 25 nt), one completely consistent with the sequence of the target gene is called small interfering RNA or siRNA, and one incompletely consistent with the sequence of the target gene is called microRNA or miRNA. Such low-molecular-weight RNA is produced from non-coding RNA upon cleavage by the RNA processing enzyme Dicer, and RNA before cleavage forms a stem-loop structure. Thereafter, the RNA binds to the target gene region, and expression control occurs by the RNA-induced silencing complex (RISC) or the like. A Dicer-like protein (CARPEL FACTORY/SUSPENSOR/SHORT INTEGUMENT) is also present in plants, and in recent years, an RNAi method has been frequently used as a tool for knocking out the expression of a specific gene in various organisms.

Generally, the flowering time of plants is influenced by environmental conditions or is already genetically determined, and most plants have a mechanism by which their flowering time is controlled such that their flowering occurs at a suitable time. This control mechanism of flowering time is influenced by developmental signals within plants, and external environmental factors such as light and temperature (Poething et al., *Science,* 250:923-930, 1990). Plants are that are sessile organisms are exposed to various environmental stresses, and thus are much influenced by the surrounding environment. Among such environmental stresses, temperature has the greatest influence on plants. There are many known plants that sense low temperature such as freezing temperature and have a wide range of temperature. When plants are exposed to temperature stress such as low temperature, they have a mechanism coinciding therewith. According to a recent report, it can be seen that plants have a clear mechanism that responds to low temperature (Sharm. P et al., *Bioessay* 27:1048-59, 2005). Many plant mechanisms that respond to a wide range of temperatures are known, and it was recently reported that a minute change in ambient temperature influences the delay of flowering at low temperatures (Fitter et al., *Science* 296:1689-91, 2002; Cook et al., *PNAS* 109:9000-5, 2012; Craufurd et al., *J. Exp. Bot.* 60:2529-39, 2009).

With respect to conventional methods for controlling flowering time, a mechanism that controls flowering time at a temperature 4° C. or below or a temperature of 37° C. or above differs from a mechanism that controls flowering time by a minute change in the ambient temperature ranging from 10° C. to 27° C., and a molecular mechanism that controls flowering time according to a change in ambient temperature has not yet been completely identified.

Accordingly, the present inventors have made extensive efforts to develop a method capable of controlling flowering time by sensing a small change in ambient temperature, from *Arabidopsis thaliana*, and as a result, have found that the SVP-FLM-β protein complex can control plant flowering by recognizing a change in ambient temperature, thereby completing the present invention.

DISCLOSURE OF INVENTION

Technical Problem

It is an object of the present invention to provide a method of controlling the flowering time of plants by inhibiting the formation of the SVP-FLM-β protein complex that is a regulating factor for flowering time capable of controlling flowering time according to a change in ambient temperature.

Another object of the present invention is to provide a method for screening a substance that inhibits the formation of the SVP-FLM-β protein complex that is a regulating factor for flowering time.

Technical Solution

To achieve the above objects, the present invention provides a method for controlling the flowering time of a plant, the method comprising regulating the formation of the SVP-FLM-β protein complex in the plant.

The present invention also provides a recombinant plant having an early flowering time, which has SVP RNAi and/or FLM-β RNAi introduced therein.

The present invention also provides a method for screening a promoting factor for flowering time, the method comprising the steps of: (a) treating a plant with a promoting factor for flowering time candidate; (b) analyzing the formation of the SVP-FLM-β protein complex based on the expression levels of SVP and FLM-β in the plant treated with the candidate; and (c) selecting the candidate as the promoting factor for flowering time, when the expression levels of SVP and FLM-β are lower than those in a control.

FIG. 2 shows the flowering times of mutants (RLN: rosette leaf number, CLN: cauline leaf number, TLN: total leaf number).

Figure 3:
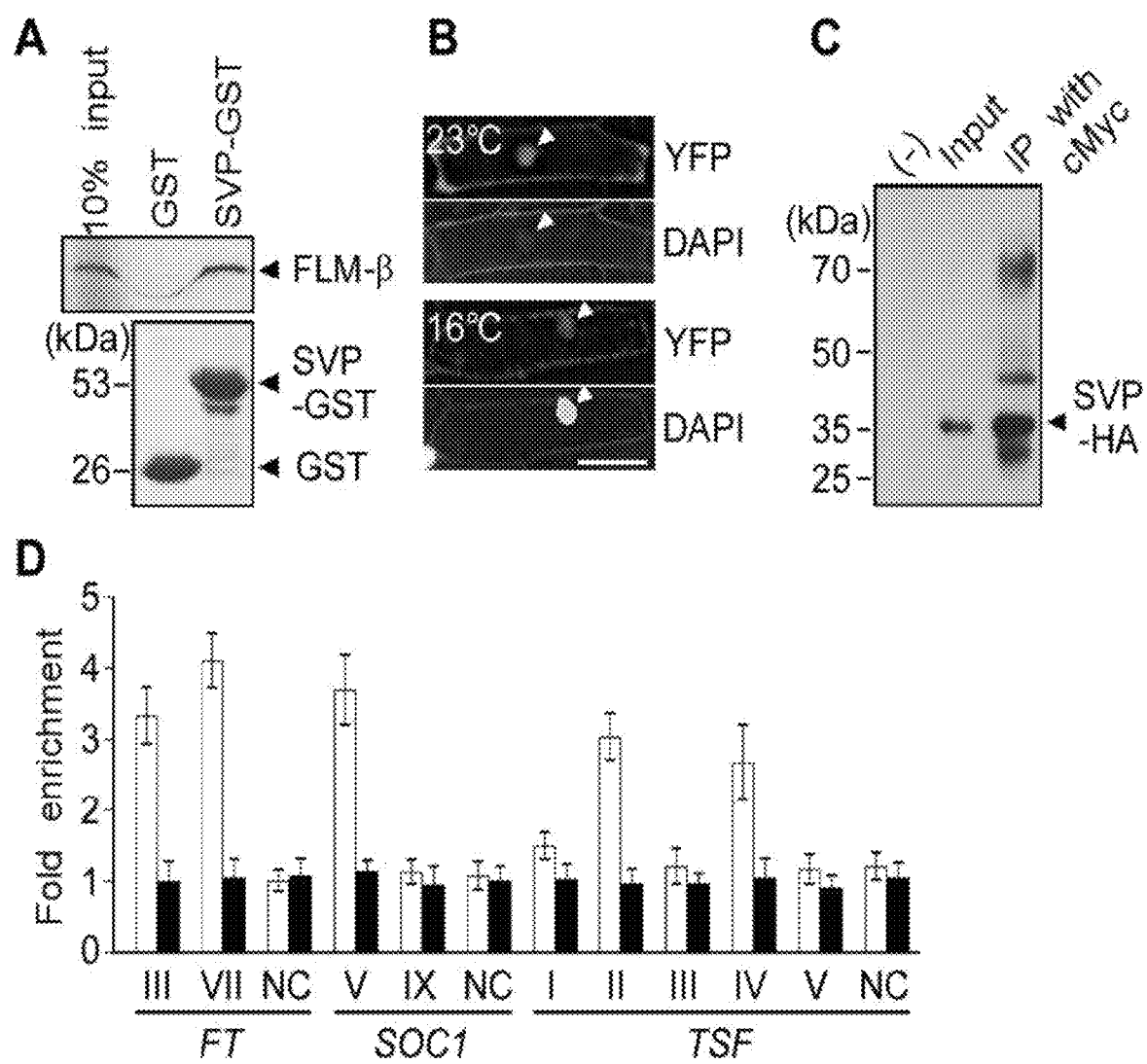

FIG. 3 shows the interaction between FLM-β and SVP proteins (A: shows the interaction between FLM-β and SVP proteins by in vitro GST pull-down analysis. SVP-GST was confirmed by Coomassie staining, and FLM-β was confirmed by labeling with $^{35}$S; B: shows the results of analyzing the expression of SVP-nYFP and FLM-β-cYFP in onion Epidermal cells by a bimolecular fluorescence complementation (BiFC) assay. The arrow indicates the nucleus, and the scale bar is 200 μm; C: shows the interaction between FLM-β and SVP proteins by co-immunoprecipitation; D: shows the results of chromatin immunoprecipitation performed to examine FLM bound to FT, SOC1 and TSF genomic regions. The chromatin immunoprecipitation was performed with pFLM:gFLM:GFP flm-3 (white) and pFLM:gFLM:GFP svp-32 flm-3 (black) at 16° C., and analysis was performed with GFP and cMyc antibody).

Figure 4:
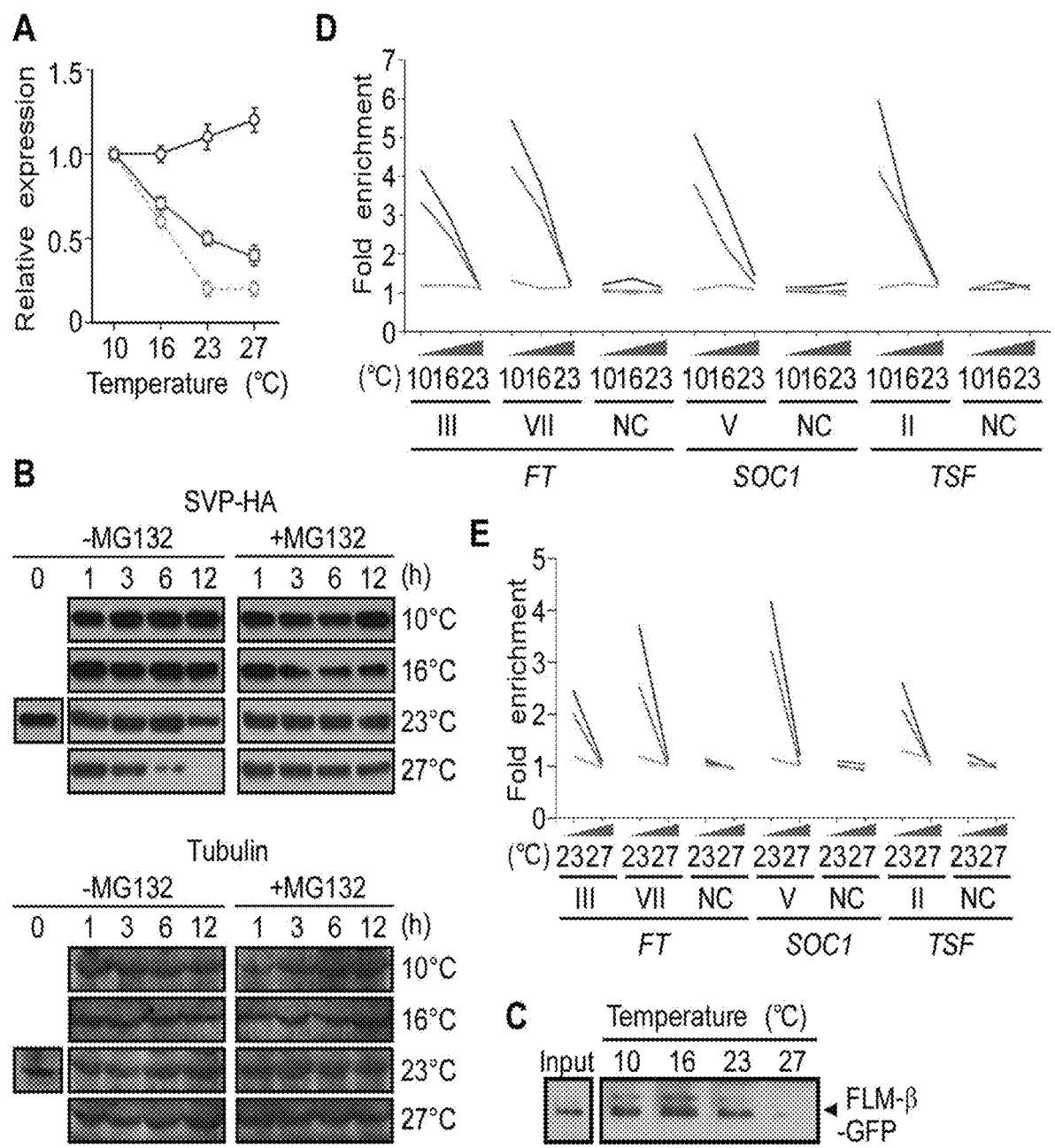

FIG. 4 shows the results of analyzing the expression of SVP and FLM-β at varying temperatures (A: shows the transcription levels of SVP (blue), FLC (purple) and FLM-β (orange color) in wild type Col at varying temperatures; B: shows the results of examining the stability of SVP at varying temperatures in (-)MG132 and (+)MG132 conditions. A pSVP:SVP:HA svp-32 plant incubated at 23° C. was treated with cycloheximide (CHX) and placed at varying temperatures, and then the amount of SVP protein in the plant was examined; C: shows the results of mutual immunoprecipitation performed to analyze the amount of the SVP-FLM-β complex at varying temperatures. SVP:HA and FLM-β-GFP were expressed temporarily in the mesophyll protoplasts of *Arabidopsis thaliana* at different temperatures and immunoprecipitated with anti-HA antibody, and immunoblotting with GFP was performed; D and show the results of chromatin immunoprecipitation performed to examine SVP bound to the FT, SOC1 and TSF genomic regions. pSVP:SVP:HA svp-32 (blue), pSVP:SVP:HA svp-32 flc-3 (purple) and pSVP:SVP:HA svp-32 flm-3 (orange color) mutants were measured at varying temperatures under long-day conditions (D) and shortday conditions (E)).

Figure 5:
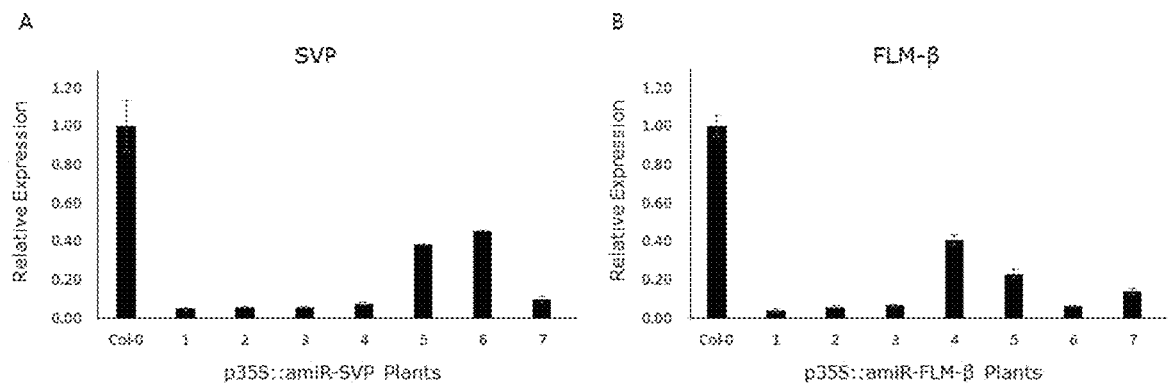

FIG. 5 shows the results of analyzing the expression of SVP and FLM-β genes in 7 miRNA transgenic plants.

Figure 6:
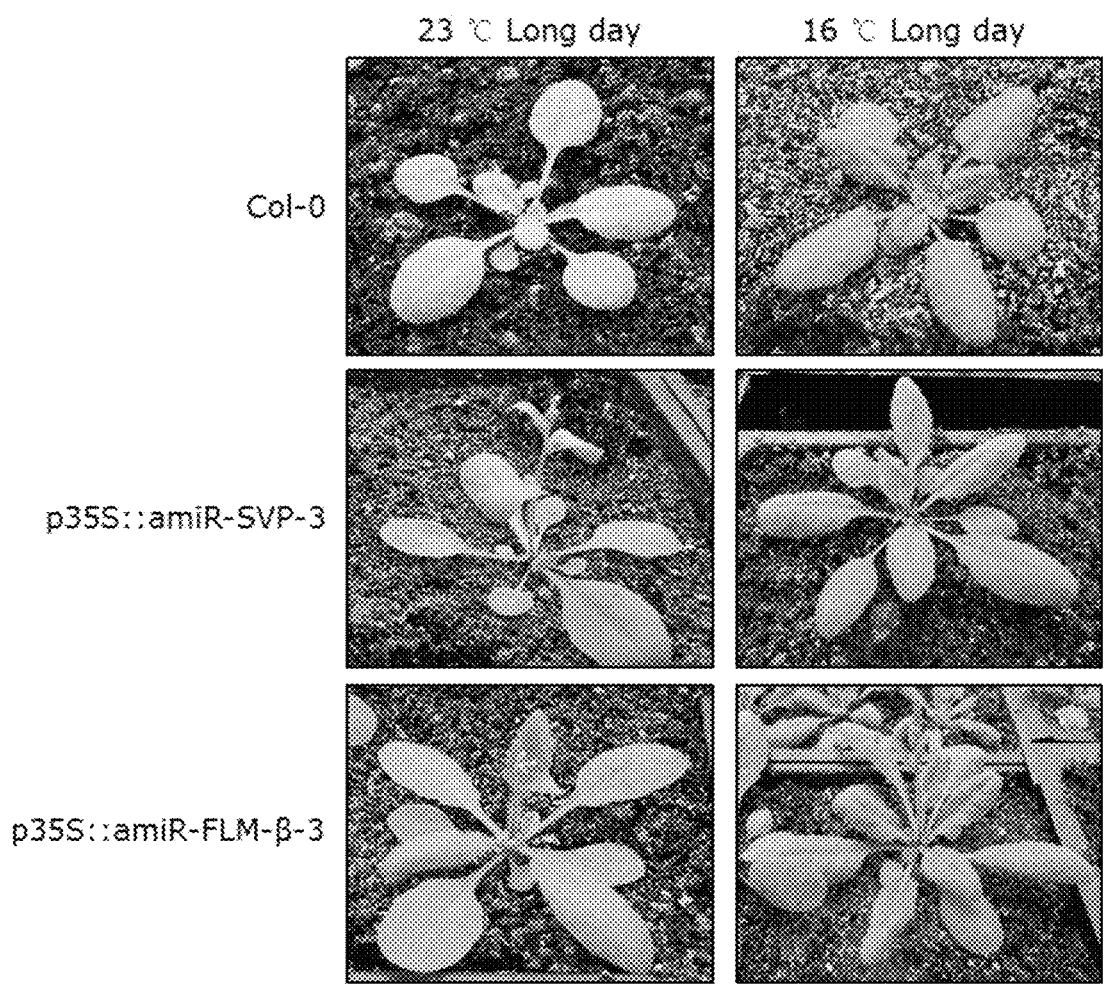

FIG. 6 is a set of photographs showing a comparison of flowering time between miRNA transgenic plants.

Figure 7:
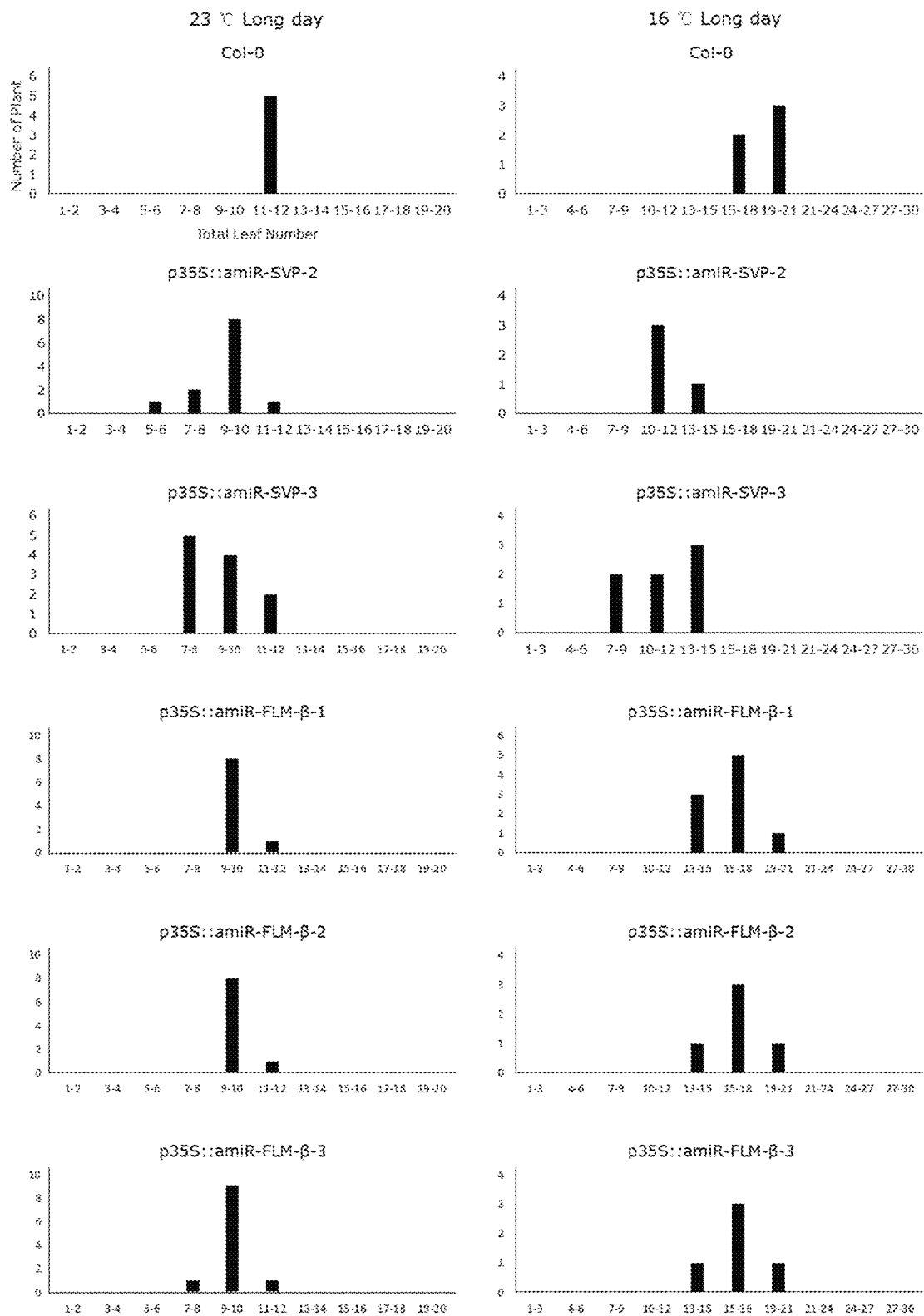

FIG. 7 shows the results of measuring the number of leaves to determine the flowering times of miRNA transgenic plants (A: SVP miRNA transgenic plant, and B: FLM-β miRNA transgenic plant).

Figure 8:
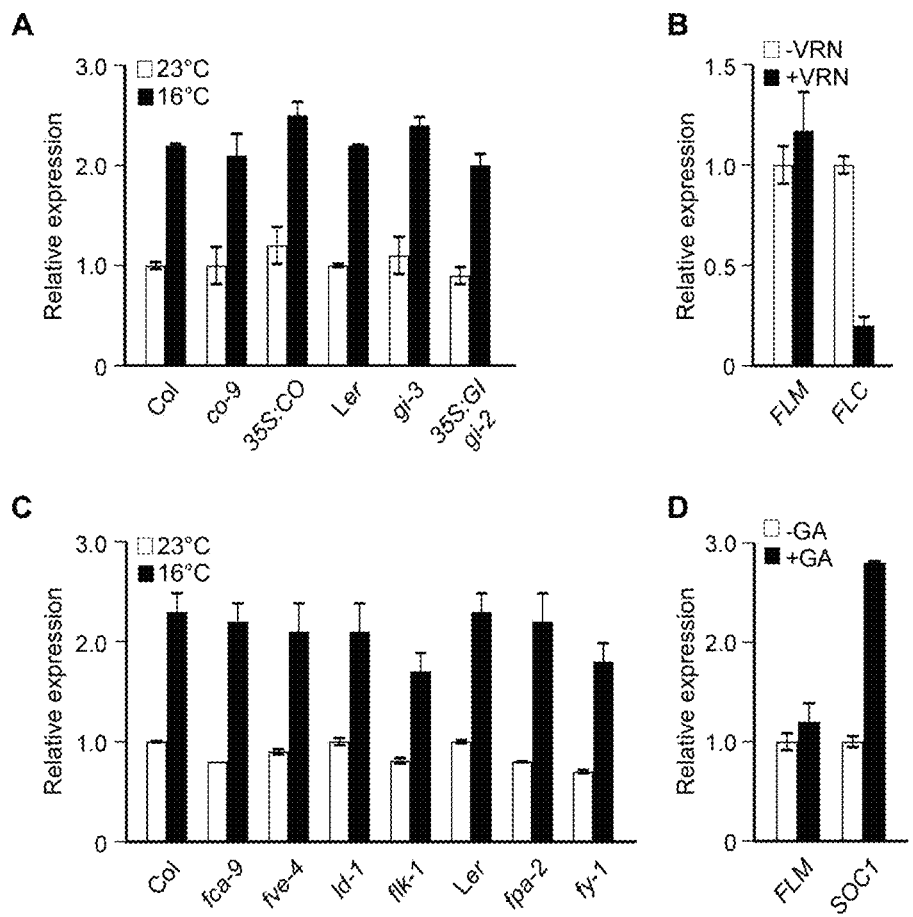

FIG. 8 shows the results of the effects of vernalization and gibberellin treatment on the expression of FLM (A and C: show the results of examining the expression of FLM in mutants; B and D: show the results of examining the expression of FLM caused by vernalization and gibberellin treatment).

Figure 9:
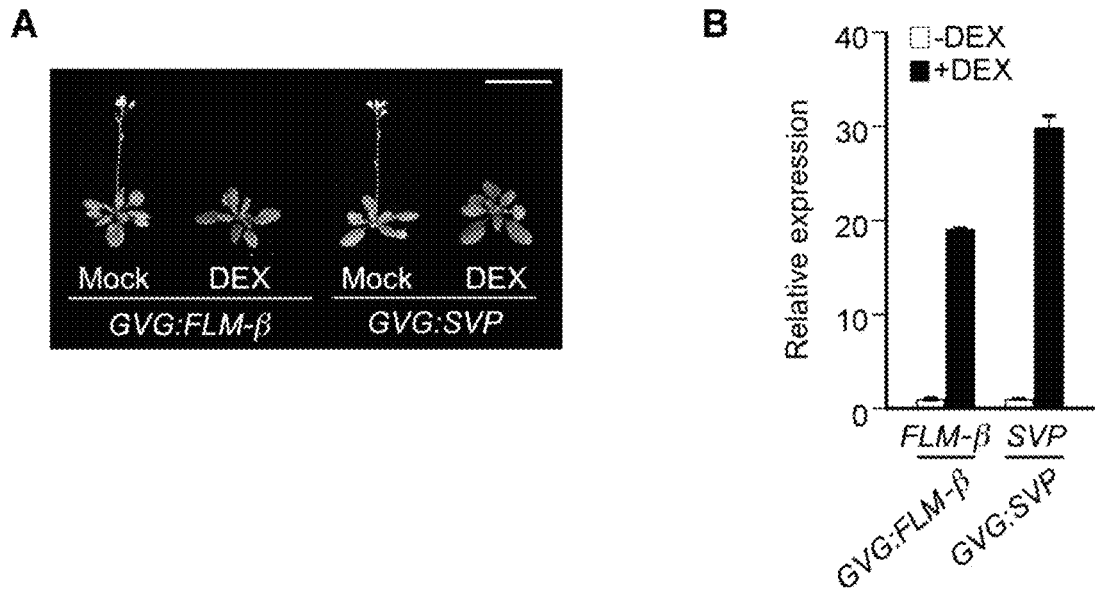

FIG. 9 shows the results of treating GVG:FLM-β and GVG:SVP transgenic plants with dexamethasone.

FIG. 10a shows primers used in cloning, ChIP-qPCR, RT-qPCT, and sequencing (SEQ ID NOs: 49 to 76); FIG. 10b shows primers used in cloning, ChIP-qPCR, RT-qPCT, and sequencing (SEQ ID NOs: 77 to 102); FIG. 10c shows primers used in cloning, ChIP-qPCR, RT-qPCT, and sequencing (SEQ ID NOs: 103 to 129); FIG. 10d shows primers used in cloning, ChIP-qPCR, RT-qPCT, and sequencing (SEQ ID NOs: 130 to 139).

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

In the present invention, in order to determine a flowering control mechanism for the perception of ambient temperature by plants and a change in ambient temperature, the expression of promoting genes for flowering promoter genes in mutants lacking the regulating factor for flowering time having sensitivity to a change in ambient temperature was analyzed, and regulating factor for flowering time that increase or inhibit the expression of the flowering promoter genes FT (Flowering locus T), SOC1 (Suppressor of Overexpression of Constans1) and TSF (Twin Sister of FT) were selected. To examine the interaction between the selected regulating factor for flowering time, various methods, including an in vitro GST pull-down assay, a bimolecular fluorescence complementation assay, co-immunoprecipitation and chromatin immunoprecipitation, were performed. As a result, it was found that FLM-β protein and SVP protein bind to each other to form a protein complex. In addition, the expression of SVP, FLM and FLC at varying temperatures was examined, and as a result, it was found that the three genes act at different temperatures.

The regulation of expression of FLM-β by a change in temperature occurred at the RNA level, but it was found that the expression of SVP was controlled at the protein level and that the SVP-FLM-β complex also decreased with a decrease in FLM-β transcripts and SVP protein by a change in temperature. In other words, it could be seen that the formation of the SVP-FLM-β protein complex was regulated by a small change in temperature. In addition, it could be seen that the SVP-FLM-β protein complex did bind to downstream flowering promoter genes such as FT, SOC1 and TSF in a temperature-specific manner to influence the expression of these genes, suggesting that the SVP-FLM-β protein complex controls flowering time by sensing a minute change in temperature.

Thus, it was found that, when the expression of SVP or FLM-β was inhibited using RNAi in order to regulate the formation of the SVP-FLM-β protein complex to control flowering time, the formation of the SVP-FLM-β protein complex was inhibited and sensitivity to temperature was reduced, thus promoting flowering. Accordingly, the present invention suggests that regulation of the formation of the SVP-FLM-β is used to prevent a decrease in the production of plants or a change in the ecosystem from being caused by a sudden change in temperature.

Thus, the present invention is directed to a method for controlling the flowering time of a plant, the method comprising regulating the formation of the SVP-FLM-β protein complex in the plant.

In the present invention, the flowering time of plants is delayed by increasing the formation of the SVP-FLM-β protein complex. The increase in the formation of the SVP-FLM-β protein complex is achieved by either introducing a substance that increases the expression of SVP and/or FLM-β into plants or treating plants with the substance.

In present invention, the flowering time of plants is promoted by inhibiting the formation of the SVP-FLM-β protein complex. The inhibition of the formation of the SVP-FLM-β protein complex is achieved by either introducing a substance that inhibits the expression of SVP and/or FLM-β into plants or treating plants with the substance.

In the present invention, the flowering time is controlled at temperature ranging from 10° C. to 27° C.

In the present invention, the substance that inhibits the expression of SVP and/or FLM-β is preferably SVP RNAi and/or FLM-β RNAi, and the RNAi is siRNA or miRNA, but is not limited thereto.

In the present invention, the SVP RNAi preferably functions to degrade an mRNA corresponding to a nucleotide sequence selected from the group consisting of SEQ ID NOs: 1 to 3 and SEQ ID NOs: 31 to 39, and the FLM-β RNAi preferably functions to degrade an mRNA corresponding to a nucleotide sequence selected from the group consisting of SEQ ID NOs: 4 to 6 and SEQ ID NOs: 40 to 48, but is not limited thereto. In the present invention, in addition to regions that are targeted by artificial miRNAs for SVP and FLM-β, additional regions in which a decrease in the expression of SVP and FLM-β by the introduction of the artificial miRNAs was expected were also selected (Table 2).

Moreover, in the present invention, the SVP RNAi is preferably an miRNA selected from the group consisting of SEQ ID NOs: 7/8; 9/10; 11/12; 13/14; 15/16; and 17/18, and the FLM-β RNAi is preferably an miRNA selected from the group consisting of SEQ ID NOs: 19/20; 21/22; 23/24; 25/26; 27/28; and 29/30, but is not limited thereto.

In the present invention, transgenic plants introduced with artificial miRNAs for SVP and FLM-β were constructed, and the degradation of SVP and FLM-β mRNA was induced. As a result, it was found that the expression of SVP and FLM-β was inhibited and the sensitivity of the transgenic plants to temperature decreased so that the flowering of the plants was promoted.

Thus, the present invention is also directed to a recombinant plant having an early flowering time, which has SVP RNAi and/or FLM-β RNAi introduced therein. In the present invention, it was attempted to ensure pure-bred lines by generation advancement of the SVP RNAi and FLM-β RNAi transgenic plants and confirm the flowering time phenotypes.

In the present invention, the SVP RNAi preferably functions to inhibit the expression of SVP gene by an miRNA selected from the group consisting of SEQ ID NOs: 7/8; 9/10; 11/12; 13/14; 15/16; and 17/18, and the FLM-β RNAi preferably functions to inhibit the expression of FLM-β gene by an miRNA selected from the group consisting of SEQ ID NOs: 19/20; 21/22; 23/24; 25/26; 27/28; and 29/30, but is not limited thereto.

Known methods for transforming a plant by introducing an RNAi vector of the present invention or using the miRNA include Agrobacteria-mediated transformation, particle gun bombardment, silicon carbide whiskers, sonication, and electroporation. Among such methods, a method based on the natural transformation system of *Agrobacterium* and a method that bombards DNA directly by a gene gun are most widely used. *Agrobacterium* has a Ti or Ri plasmid, and the plasmid has genes that can be introduced into plants as foreign genes. *Agrobacterium* vector systems and methods for *Agrobacterium*-mediated gene transfer are described in a number of literatures such as Moloney et al., *Plant Cell Reports* 8:238(1989).

As used herein, the term "recombinant" indicates a cell that replicates a heterologous nucleic acid, expresses the nucleic acid or expresses a peptide, heterologous peptide, or protein encoded by a heterologous nucleic acid. Recombinant cells can express genes or gene fragments, which are not found within the native form of the cell, in either the sense or antisense form. Recombinant cells can also express genes that are found in the native form of the cell, but wherein the genes are modified and re-introduced into the cell by artificial means.

As used herein, the term "vector" refers to a means by which a foreign gene is introduced into a suitable host cell so that it can be expressed. Examples of the vector include a plasmid vector, a cosmid vector, a bacteriophage vector, and a virus vector such as an adenovirus vector, a retrovirus vector or an adeno-associated virus vector, with the plasmid vector being preferred. Among vectors developed to transform plant cells, a binary vector is most frequently used. The binary vector consists of two plasmids, in which one plasmid of the two plasmids contains a gene required for *Agrobacterium* infection and a gene required for transfer of T-DNA, and another plasmid contains T-DNA in which the target gene can be inserted. The latter can be constructed such that it can be replicated in *E. coli* and *Agrobacterium* in a chromosome-independent manner, has an antibiotic resistance gene, and has both end regions (left border (LB) and right border (RB)) of T-DNA essential for gene transfer into plant cells. A variety of binary vectors are known in the art.

As used herein, the term "plant" is meant to include all a mature plant, and a plant cell, a plant tissue and a plant seed, which can develop into a mature plant. A plant to which the method of the present invention can be applied may be a dicotyledonous plant, but is not limited thereto. The dicotyledonous plant is preferably *Arabidopsis thaliana*, but is not limited thereto. Examples of plants whose flowering can be controlled by the method of the present invention include food crops, including rice, wheat, barley, maize, bean, potato, red-bean, oat and Indian millet plants; vegetable crops, including Chinese cabbage, radish, red pepper, strawberry, tomato, watermelon, cucumber, cabbage, melon, pumpkin, stone-leek, onion, and carrot; crops for special use, including ginseng, tobacco, cotton plant, sesame, sugar cane, sugar beet, *Perilla japonica*, peanut, and rape; fruit trees, including apple tree, pear tree, jujube tree, peach, kiwi, grape, citrus, persimmon, plum, apricot, and banana; flowering plants, including rose, gladiolus, gerbera, carnation, chrysanthemum, lily, and tulip; and feed crops, including rye grass, red clover, orchard grass, alfalfa, tall fescue, and perennial ryegrass.

The present invention is also directed to a method for screening a promoting factor for flowering time, the method comprising the steps of: (a) treating a plant with a promoting factor for flowering time candidate; (b) analyzing the formation of the SVP-FLM-β protein complex based on the expression levels of SVP and FLM-β in the plant treated with the candidate; and (c) selecting the candidate as the promoting factor for flowering time, when the expression levels of SVP and FLM-β are lower than those in a control.

EXAMPLES

Hereinafter, the present invention will be described in further detail with reference to examples. It will be obvious to a person having ordinary skill in the art that these examples are illustrative purposes only and are not to be construed to limit the scope of the present invention.

Plant Material and Growth Conditions

All mutants used in the present invention are referred to as Columbia (Col) background and are not mentioned otherwise. Wild-type seeds were obtained from the *Arabidopsis* Biological Resource Center (ABRC). 35S:CO, 35S:GI, gi-2, gFLM:GUS, gSVP:GUS, co-9, flc-3, flm-1(Ws), flm-3, fca-9, flk-1, fpa-2, ft-10, fve-4, fy-1(Ler), gi-3(Ler), ld-1, soc1-2, svp-32 and tsfl-were obtained by a previously known method (Michaels et al., *Plant Cell* 11:949-956, 1999; Balasubramanian et al., *PLoS Genet* 2:e106, 2006; Scortecci et al., *Plant J.* 26:229-236, 2001; Lee et al., *Genes Dev.* 21:397-402, 2007; Baurle et al., *Science* 318:109-112, 2007; Lim et al., *Plant Cell* 16:731-740, 2004, Lee et al., *Plant Cell* 6:75-93, 1994; Simpson et al., *Cell* 113:777-787, 2003; Schomburg et al., *Plant Cell* 13:1427-1436, 2001; Kim et al., *Nat. Genet.* 36:167-171, 2004; Ausin et al., *Nat. Genet.* 36:162-166; Lee et al., *Genes Dev.* 14:2366-2376, 2000; Tamaguchi et al., *Plant Cell Physiol.* 46:1175-1189; Yoo et al., *Plant Physiol.* 139:770-778, 2005).

The homozygosity of double mutants was confirmed by PCR genotyping. Wild-type, mutants and transgenic plants were grown in soil or MS medium at temperatures of 27, 23, 16, 10 and 5° C. under long-day (LD) conditions (16-hr light/8-hr dark) or short-day (SD) conditions (9-hr light/15-hr dark) in which light was provided at an intensity of 20 µmol m$^{-2}$ s$^{-1}$. Flowering time was measured by scoring the total number of leaves.

Vernalized seeds were stored at 4° C. for 4 weeks, and then grown in soil or MS medium at 23° C. under long-day conditions. Gibberellin-treated seeds were grown in soil or MS medium at 23° C. under short-day conditions, and when the seeds were germinated, 100 µM GA$_3$ solution was sprayed to the plant every week until the plant flowered. In a temperature-shift experiment, plants cultivated at 23° C. for 6 days were shifted to 10° C., 16° C. or 27° C. and cultivated for 2 days (FIG. 8).

Transgenic Plants pSVP:SVP:HA was constructed by amplifying the ORF of SVP by PCR and cloning the amplification product into a pCHF3 vector containing an 2.5 kb SVP promoter. GVG:FLM-β and GVG:SVP were constructed by amplifying the ORF of each gene by PCR and cloning the amplification product into a pTA7002 vector. The pTA7002 vector was used to induce GVG(GAL4-VP16-GR) with dexamethasone in order to express the target gene (Aoyama et al., *Plant J.* 11:605-612, 1997). 35S:SVP:HA was constructed by amplifying the SVP:HA region of pSVP:SVP:HA by PCR and cloning the amplification product into a pCHF3 vector. Plants were transformed using a modified floral dip method (FIG. 9).

Sequencing of Genomic FLM

Genomic DNA was extracted using a plant DNA extraction kit (GeneAll, Korea). In order distinguish FLM-β from FLM-6 transcripts, a 1.5-kb genome fragment (from intron 1 to exon 4) was amplified by PCR using Phusion DNA taq polymerase (NEB, USA), and then the nucleotide sequence thereof was analyzed. The nucleotide sequence and GenBank accession number of wild-type FLM are as follows: KF49688(Ler), KF496889(An-1), KF49690(JI-3), KF496891(KZ-9), KF49692(Tsu-0), KF496893(Rubezhnoe-1), KF49694(En-1), KF496895(Li-5), KF49696(Bla-2), KF496897(Sei-0), KF49698(Mh-0) KF496899(Gr-3).

Example 1

Figure 1:
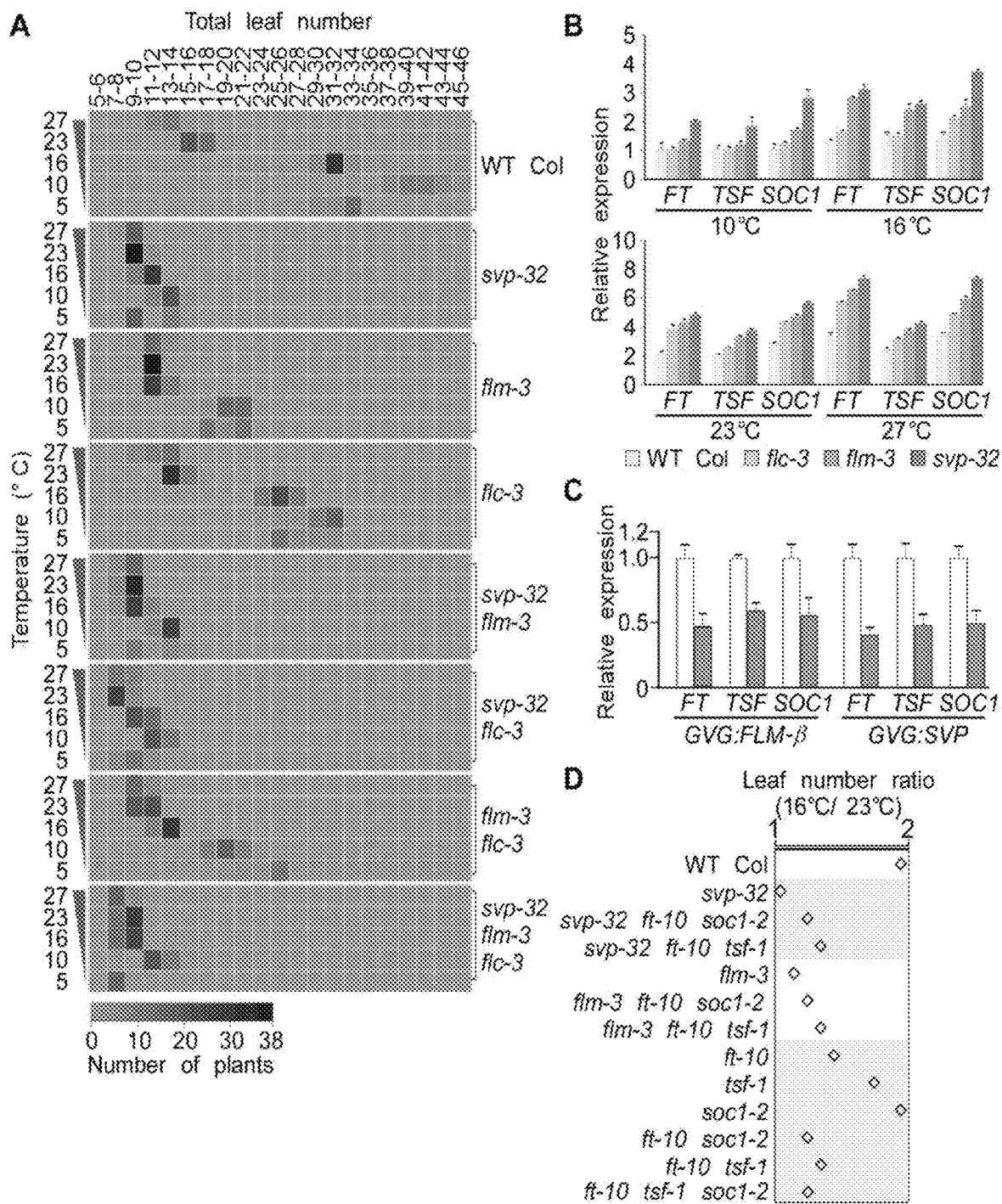
FIG. 1 shows the flowering times and the gene expression of mutants (A: shows the flowering times of svp-32, flm-3 and 20 flc-3 mutants, double mutants and triple mutants at varying temperatures; B: shows the expression of FT, SOC1 and TSF genes in svp-32, flm-3 and flc-3 mutants; C: shows the expression of FT, SOC1 and TSF at 8 hours after treatment of GVG:FLM-β and GVG:SVP plants with 30 μM dexamethasone (DEX); D: shows the leaf number ratio (16° C./23° C.) of svp-32, flm-3 and flc-3 Single mutants, double 5 mutants and triple mutants).

Examination of Flowering Time of Mutants that Lack Regulating Factor for Flowering Time, and Analysis of Expression of Flowering Promoter Gene 1-1: Examination of Flowering Time of Mutants In a first step of determining a signaling mechanism for the recognition of ambient temperature by plants and a change in ambient temperature, mutants lacking a regulating factor for flowering time having sensitivity to a change in ambient temperature were selected. The flowering times of flm, flc and svp mutants at a temperature of 5° C. to 27° C. (daily temperature range) were examined (FIG. 1A).

As a result, the flowering of wild-type *Arabidopsis thaliana* was delayed, but the svp-32 mutant flowered in the entire temperature range (FIG. 1A), flm-3 flowered in the temperature range excluding a temperature of 10° C. or below, and flc-3 showed delayed flowering only at a temperature of 16° C. or below. This indicates that SVP acts in a broad temperature range (5° C. to 27° C.) and the MADS box proteins FLM, FLC and SVP act at different temperatures.

In addition, it was shown that double mutants and triple mutants, which include the svp mutant, flowered in the temperature range of 5° C. to 27° C., suggesting that SVP has the greatest effect on the control of flowering time compared to the two other genes (FIG. 2).

1-2: Analysis of Expression of Flowering Promoter Gene in Mutants

For real-time quantitative PCR analysis, RNA was isolated from *Arabidopsis thaliana* using an RNA purification reagent (Invitrogen, USA). The RNA used had A260/A230>2.0 and A260/A230>1.8, as measured by a Nanodrop ND-200 spectrophotometer (Nanodrop Technologies). To remove DNA contaminants, the RNA sample was treated with DNaseI (NEB, USA) at 37° C. for 60 minutes. 1-2 µg of the RNA was used to synthesize cDNA, and real-time quantitative PCR analysis was performed by LightCycler 480 (Roche Applied Science, USA) using a Roche SYBR Green Master mixture (Roche Applied Science, USA). As reference genes, PP2AA3 and SAND family proteins were used. In addition, GVG (GAL4-VP16-GR) in GVG:FLM-β and GVG:SVP plants was induced with dexamethasone to express the target gene, and then the expression of the flowering promoter gene was analyzed.

As a result, it was shown that the expression of the flowering promoter genes (FT, TSF and SOC1) in the mutants lacking the regulating factor for flowering time having a sensitivity to a change in ambient temperature was high in the entire temperature range (10° C. to 27° C.) for in svp-32, high at 16° C. to 27° C. for in flm-3, and high at 23° C. to 27° C. for flc-3 (FIG. 1B). Also, a decrease in the expression of the flowering promoter genes in the plant treated with dexamethasone could be observed.

Example 2

Analysis of Interaction Between Regulating Factors for Flowering

In this Example, the interaction between FLM-β protein and SVP protein was analyzed.

2-1: Yeast Two-Hybrid Analysis

Yeast two-hybrid analysis was performed according to a previously described method by amplifying the ORFs of FLC, FLM-β and SVP by PCR and cloning the amplification product into a pGADT7 or pGBKT7 vector (Clontech, USA) (Lee et al., *Plant Sci.* 185-6:97-104, 2012).

As a result, the binding between FLM-β and SVP proteins in SD/-Trp/-Leu medium and SD/-Trp/-Leu/-His/X-gal medium was confirmed.

2-2: In Vitro GST Pull-Down Analysis

To perform in vitro GST pull-down analysis, SVP ORF was cloned into a pGEX-5x-1 vector (Amersham Phamacia Biotech, USA), and then the production of a SVP-GST fusion protein at 20° C. was induced by IPTG in *E. coli* BL21(DE3). The water-soluble GST fusion protein was fixed to a glutathione sepharose bead (GE Healthcare, USA). FLM-β ORF was cloned into a pGEM vector, and then subjected to in vitro translation together with $^{35}$S using a TNT T7 Quick Coupled transcription/translation system (Promega, USA). The translation product was reacted with the GST fusion protein fixed to the glutathione sepharose bead.

As a result, the interaction between FLM-β and SVP protein was confirmed (FIG. 3A).

2-3: Bimolecular Fluorescence Complementation Analysis

For bimolecular fluorescence complementation analysis, genes encoding the FLM-β and SVP proteins were cloned into pUC-SPYNE/pSPYNE-35S and pUC-SPYCE/pSPYCE-35S vectors (Walter et al., *Plant J.* 40:428-438, 2004). The SVP-nYFP and FLM-β-cYFP fusion proteins were delivered into onion epidermal cells using a DNA particle delivery system (PDS-1000/He; Bio-Rad, USA). The cells were incubated in MS medium at 23° C. and 16° C. for 16-24 hours under dark conditions, and then observed with a confocal microscope (Carl Zeiss, Germany).

As a result, SVP fused to the N terminus of YFP (yellow fluorescence protein) expressed in the onion nucleus and FLM-β fused to the C terminus of YFP were observed at 23° C. and 16° C. (FIG. 3B).

2-4: Co-Immunoprecipitation Analysis

Co-immunoprecipitation in tobacco leaves was performed according to a previously described method (Voinnet et al., *Plant J.* 33:949-956, 2003), and co-immunoprecipitation in *Arabidopsis thaliana* protoplasts was also performed according to a previously described method (Lee et al., *Plant Cell Physiol.* 53:1802-1814, 2012). 35S:SVP:HA and 35S:FLM-β:GFP plasmid DNAs were expressed temporarily in the mesophyll protoplasts of *Arabidopsis thaliana*, and after 6 hours, the plant tissue was treated with 100 µM cycloheximide (CHX) and then incubated at 27° C., 23° C., 16° C. and 10° C. for 14 hours. The incubated material was centrifuged at 13,000×g at 4° C. for 15 minutes, and the extracted protein supernatant was reacted with anti-HA antibody (Sigma, H9658). The reaction product was mixed with an A/G PLUS-agarose bead (Santa Cruz,sc-2003) and reacted at 4° C. for 2 hours, and then analyzed.

As a result, the interaction between FLM-β and SVP was confirmed once more (FIG. 3C), suggesting that FLM-β and SVP bind to each other to control flowering according to a change in ambient temperature.

2-5: Chromatin Immunoprecipitation (ChIP) Analysis

The binding of FLM protein and SVP protein to the genomic regions of FT, TSF and SOC1 genes was analyzed. The pFLM:gFLM:GFP, pSVP:gSVP:HA and 35S:SVP:HA cells incubated in soil or MS medium under varying temperature conditions and light conditions were fixed with formaldehyde. Nucleic acid extraction and immunoprecipitation analysis were performed according to a previously described method (Kim et al., *Plant Physiol.* 159:461-478, 2012), and chromatin was cut by sonication and analyzed with GFP and cMyc antibody.

As a result, it was shown that the amount of the FLM-β and SVP proteins binding to the genomic regions of the FT, TSF and SOC1 genes in the flm-3 and svp-32 mutants and double mutants decreased (FIG. 3D). This suggests that FLM-β and SVP binds to each other to control flowering according to a change in ambient temperature.

Example 3

Analysis of Expression of FLM-β and SVP

For measurement of the expression of wild-type SVP, FLC and FLM-β, the transcription level thereof at each temperature was analyzed by RT-qPCR. Also, analysis of the stability of SVP protein was performed by allowing a pSVP:SVP:HA svp-32 plant to grow in MS medium at 23° C. under long-day or short-day conditions, treating the grown plant with 100 µM CHX for 30 minutes, shifting the treated plant to varying temperatures (27° C., 23° C., 16° C. and 10° C.), and incubating the plant in the presence of 10 µM MG132 proteasome inhibitor. FT, whose protein level is stable at high temperature, was used as a control protein.

As a result, it was shown that the FLM-β and FLC transcripts decreased with an increase in temperature, but the transcription level of SVP did not change even when temperature increased (FIG. 4A). However, it was found that the SVP protein decreased at high temperature (FIG. 4B), and was degraded within 12 hours at high temperature and the degradation thereof was inhibited by the proteasome inhibitor MG132 (FIG. 4B). In addition, it was shown that, as FLM-β transcripts and SVP protein were decreased by a change in temperature, the SVP-FLM-β complex also decreased (FIG. 4C).

Example 4

Analysis of the Binding of SVP Protein to Genomic Region of Flowering Promoter Gene The binding of SVP protein to the genomic region of FT, TSF and SOC1 genes in pSVP:SVP:HA svp-32, pSVP:SVP:HA svp-32 flc-3 and pSVP:SVP:HA svp-32 flm-3 mutants was analyzed by chromatin immunoprecipitation (FIGS. 4D and 4E).

As a result, it was shown that the binding of SVP to the genome of the flowering promoter genes were high at low temperature (10° C.) under long-day conditions, but the SVP protein did not bind to the flm mutant, and the binding of the SVP protein to the flc decreased by an average of 24.7%. Also, it was shown that the binding of the SVP protein increased by about 3 times at low temperature under short-day conditions (FIG. 4E). In addition, when FLM lost its activity, the binding of the SVP protein to the target gene was inhibited, indicating that the SVP-FLM-β complex is a major mediator that controls flowering by sensing a change in ambient in the temperature range of 10° C. or to 27° C.

Example 5

Construction of Artificial miRNA Transgenic Plants

In this Example, a double-stranded RNA consisting of a sense, which has a sequence homologous to the mRNA of the target genes SVP and FLM-β, and an antisense having a sequence complementary thereto, was introduced into a plant to induce degradation of the mRNA-targeting regions of the target genes, thereby inhibiting the expression of the target genes SVP and FLM-β.

Using a pRS300 vector as a template, 572 bp target regions of SVP and FLM-β genes were amplified by PCR using primers (Table 1). The 572 bp amplification products were cloned into pBluescriptSKII(+) vectors, and then sequenced. Next, the cloned inserts were digested by KpnI/BamHI restriction enzymes, and then cloned again into the plant transformation vector pCHF3.

In order to construct transgenic *Arabidopsis thaliana* that expresses p35S::amiR-SVP or p35S::amiR-FLM-β, an *Agrobacterium tumefaciens* GV3101 strain having each of the vectors constructed as described above was incubated in an YEB medium containing 100 mg/L of spectinomycin at 28° C. for 3 days. Then, for p35S::amiR-SVP or p35S::amiR-FLM-β, wild-type *Arabidopsis thaliana* (ecotype Columbia) was transformed by the floral dip method. All the transgenic plants were selected in MS medium containing 100 mg/L of kanamycin and were incubated at 23° C. and 16° C. under long-day conditions (16-hr light/8-hr dark cycle) in which light was provided at an intensity of 120 µmol m$^{-2}$s$^{-1}$, thereby constructing artificial miRNA transgenic plants.

TABLE 1

Target regions and primers used in construction of artificial miRNA transgenic plants

| Constructs | Target regions (5'→3') | Primers (5'→3') |
|---|---|---|
| p35S::amiR-SVP-1 | TTGTGTAAGTTT CTGCCTATG (SEQ ID NO: 1) | TATAGGCAGAAACTTACACAG (SEQ ID NO: 7) CTGTGTAAGTTTCTGCCTATA (SEQ ID NO: 8) CTATGTAAGTTTCAGCCTATT (SEQ ID NO: 9) AATAGGCTGAAACTTACATAG (SEQ ID NO: 10) |
| p35S::amiR-SVP-2 | TCGTCGGAGTCT ATTACTAAC (SEQ ID NO: 2) | TTTAGTAATAGACTCCGACGA (SEQ ID NO: 11) TCGTCGGAGTCTATTACTAAA (SEQ ID NO: 12) TCATCGGAGTCTAATACTAAT (SEQ ID NO: 13) ATTAGTATTAGACTCCGATGA (SEQ ID NO: 14) |
| p35S::amiR-SVP-3 | CAGTGATCACGC CCGAATGAG (SEQ ID NO: 3) | TTCATTCGGGCGTGATCACTT (SEQ ID NO: 15) AAGTGATCACGCCCGAATGAA (SEQ ID NO: 16) AAATGATCACGCCGGAATGAT (SEQ ID NO: 17) ATCATTCCGGCGTGATCATTT (SEQ ID NO: 18) |
| p35S::amiR-FLM-β-1 | AAGCCTGATTCA TAATTAAGA (SEQ ID NO: 4) | TCTTAATTATGAATCAGGCGT (SEQ ID NO: 19) ACGCCTGATTCATAATTAAGA (SEQ ID NO: 20) |

TABLE 1 -continued

Target regions and primers used in construction of artificial miRNA transgenic plants

| Constructs | Target regions (5'→3') | Primers (5'→3') |
|---|---|---|
| | | ACACCTGATTCATTATTAAGT (SEQ ID NO: 21) ACTTAATAATGAATCAGGTGT (SEQ ID NO: 22) |
| p35S::amiR-FLM-β-2 | ATGATGGAGTAT ATCGAGTCC (SEQ ID NO: 5) | TGACTCGATATACTGCGTCAT (SEQ ID NO: 23) ATGACGCAGTATATCGAGTCA (SEQ ID NO: 24) ATAACGCAGTATAACGAGTCT (SEQ ID NO: 25) AGACTCGTTATACTGCGTTAT (SEQ ID NO: 26) |
| p35S::amiR-FLM-β-3 | CTGCTCTGTCCG TAAGTAGAG (SEQ ID NO: 6) | TTCTACTTACGGATAGCGCAG (SEQ ID NO: 27) CTGCGCTATCCGTAAGTAGAA (SEQ ID NO: 28) CTACGCTATCCGTTAGTAGAT (SEQ ID NO: 29) ATCTACTAACGGATAGCGTAG (SEQ ID NO: 30) |

Example 6

Analysis of Flowering Time of miRNA Transgenic Plants

The expression of SVP and FLM-β genes in the miRNA transgenic plants constructed in Example 5 was analyzed by RT-qPCR. For RT-qPCR, total RNA was extracted from the transgenic plants using Trizol reagent, and then subjected to a reverse transcription reaction using a first-strand cDNA synthesis kit (Thermo Scientific, USA) and oligo-dT primers. The synthesized first-strand cDNA was used together with the housekeeping genes PP2A A3 and SAND, and gene-specific primers in the RT-qPCR analysis of SVP and FLM-β.

As a result, decreases in the expression of SVP and FLM-β genes in each of the transgenic plants could be seen (FIG. 5).

The flowering times of the transgenic plants that express p35S::amiR-SVP and p35S::amiR-FLM-β were measured at 23° C. and 16° C. under long-day conditions.

As a result, it could be seen that the flowering time of the transgenic plants corresponding to p35S::amiR-SVP-1 was similar to the wild-type plant, but p35S::amiR-SVP-2/-3 and p35S::amiR-FLM-β-1/-2/-3 transgenic plants had early flowering times compared to the wild-type plant and showed a phenotype insensitive to temperature (FIGS. 6 and 7).

In addition to the regions targeted by the microRNA of the present invention, additional target regions of SVP and FLM-β genes were also analyzed (Table 2).

TABLE 2

Additional regions of SVP and FLM-β in which decreases in expression by artificial miRNAs for SVP and FLM are expected

| Gene | Target regions (5'→3') | Gene | Target regions (5'→3') |
|---|---|---|---|
| SVP | CTGCATTTCTGGTTAGTAACG (SEQ ID NO: 31) | FLM-β | GAGTATATCGAGTCCCTTAAA (SEQ ID NO: 40) |

TABLE 2-continued

Additional regions of SVP and FLM-β in which decreases in expression by artificial miRNAs for SVP and FLM are expected

| Gene | Target regions (5'→3') | Gene | Target regions (5'→3') |
|---|---|---|---|
| | ACGCTTGTCACCGATAAACTT (SEQ ID NO: 32) | | AAGCTCGACAACTTTCGATTC (SEQ ID NO: 41) |
| | AAGAGACAATGTCTAAGTAGT (SEQ ID NO: 33) | | GTGTCTGAATGTACGGATTGG (SEQ ID NO: 42) |
| | TAGGCTCGGCTTACCGTATGG (SEQ ID NO: 34) | | ATGGGAAAGAATACGTTGCTG (SEQ ID NO: 43) |
| | AAGTCCTAGAGAGGCATAACT (SEQ ID NO: 35) | | TAGGGCATAACCCTTATCGGA (SEQ ID NO: 44) |
| | GAGCGACTTGGCATGCAAATA (SEQ ID NO: 36) | | TTGTGTCTGAATGTACGGATT (SEQ ID NO: 45) |
| | CAGCAAGGAACGCAACTAACG (SEQ ID NO: 37) | | TTGTACCTCCTTCGGAGACAA (SEQ ID NO: 46) |
| | TCGGCTTACCGTATGGTGGTT (SEQ ID NO: 38) | | ACGGCTGAGTTTTCACCTTAA (SEQ ID NO: 47) |
| | TCGGAGAACGCTGCTGTGTAC (SEQ ID NO: 39) | | GAGCTAGGAAGGCAGAACTGA (SEQ ID NO: 48) |

INDUSTRIAL APPLICABILITY

The FLM-β RNAi and SVP RNAi for controlling flowering time according to the present invention can be used to control flowering time by inhibiting the expression of FLM-β and SVP or regulating the interaction therebetween. Thus, they can prevent a decrease in crop production or a change in the ecosystem from being caused by a sudden change in temperature.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for promoting the flowering time of a plant, the method comprising inhibiting the expression of Short Vegetative Phase (SVP) gene by introducing a vector for expressing an artificial double-stranded miRNA of sense and antisense nucleotide sequences corresponding to nucleotide sequences of sense/antisense pairs selected from the group consisting of SEQ ID NOs: 11/12; 13/14; 15/16; and 17/18, wherein the artificial double-stranded miRNA degrades mRNA expressed by the Short Vegetative Phase (SVP) gene corresponding to the nucleotide sequence of SEQ ID NO: 2 or 3.

2. The method of claim 1, wherein the flowering time is promoted at atmospheric temperature ranging from 10° C. to 27° C.

* * * * *

UNITED STATES PATENT AND TRADEMARK OFFICE
CERTIFICATE OF CORRECTION

PATENT NO.        : 10,717,984 B2
APPLICATION NO.   : 14/484816
DATED             : July 21, 2020
INVENTOR(S)       : Ji Hoon Ahn Page 1 of 1

It is certified that error appears in the above-identified patent and that said Letters Patent is hereby corrected as shown below:

In the Specification

Column 3, Line 43: "D and show the results" should be -- D and E show the results --.

Signed and Sealed this
First Day of September, 2020

Andrei Iancu
*Director of the United States Patent and Trademark Office*